(12) United States Patent
Chen et al.

(10) Patent No.: US 7,820,670 B2
(45) Date of Patent: Oct. 26, 2010

(54) 6-AMINOIMIDAZO[1,2-B]PYRIDAZINE ANALOGS AS RHO KINASE INHIBITORS FOR THE TREATMENT OF RHO KINASE-MEDIATED DISEASES AND CONDITIONS

(75) Inventors: Hwang-Hsing Chen, Fort Worth, TX (US); Andrew Rusinko, Arlington, TX (US); Mark R. Hellberg, Arlington, TX (US); Bryon S. Severns, Arlington, TX (US); Alan J. Henderson, Albany, NY (US); Cheng Guo, Schenectady, NY (US); Mark Hadden, Albany, NY (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 11/960,476

(22) Filed: Dec. 19, 2007

(65) Prior Publication Data

US 2008/0153813 A1    Jun. 26, 2008

Related U.S. Application Data

(60) Provisional application No. 60/871,422, filed on Dec. 21, 2006.

(51) Int. Cl.
*A61K 31/501* (2006.01)
(52) U.S. Cl. .................................. 514/252.06
(58) Field of Classification Search ............. 514/252.06
See application file for complete search history.

(56) References Cited

U.S. PATENT DOCUMENTS

| | | | |
|---|---|---|---|
| 5,798,380 A | 8/1998 | Kaufman et al. | |
| 6,110,912 A | 8/2000 | Kaufman et al. | |
| 6,218,410 B1 | 4/2001 | Uehata et al. | |
| 6,271,224 B1 | 8/2001 | Kapin et al. | |
| 6,403,590 B1 | 6/2002 | Hellberg et al. | |
| 6,451,825 B1 | 9/2002 | Uehata et al. | |
| 6,579,519 B2 * | 6/2003 | Maitra et al. ............. | 424/78.04 |
| 6,586,425 B2 | 7/2003 | Kaufman et al. | |
| 6,649,625 B2 | 11/2003 | Azuma et al. | |
| 6,673,812 B1 | 1/2004 | Azuma et al. | |
| 6,720,341 B2 | 4/2004 | Moriyama et al. | |
| 6,794,398 B1 | 9/2004 | Nakamuta et al. | |
| 2002/0045585 A1 | 4/2002 | Kaufman et al. | |
| 2003/0220376 A1 * | 11/2003 | Masferrer et al. ........... | 514/359 |
| 2007/0049591 A1 * | 3/2007 | Pinkerton et al. ........ | 514/234.5 |

FOREIGN PATENT DOCUMENTS

| | | | |
|---|---|---|---|
| EP | 1034793 | | 9/2000 |
| WO | 99/23113 | | 5/1999 |
| WO | 01/68608 | | 9/2001 |
| WO | WO 02/066481 | * | 8/2002 |
| WO | 02/096318 | | 12/2002 |
| WO | 02/100833 | | 12/2002 |
| WO | 03/059913 | | 7/2003 |
| WO | 03/062227 | | 7/2003 |
| WO | 2004/000318 | | 12/2003 |
| WO | 2004/009555 | | 1/2004 |
| WO | 2004/024717 | | 3/2004 |
| WO | 2004/084824 | | 10/2004 |
| WO | 2004/085409 | | 10/2004 |
| WO | 2007/025090 | | 3/2007 |

OTHER PUBLICATIONS

Bullock, Structural Basis of Inhibitor Specificity of the Human Protooncogene Proviral Insertion Site in Moloney Murine Leukemia Virus (PIM-1) Kinase, J. Med. Chem. vol. 48, 7604-7614, 2005.*
Adachi et al., "Studies on Pyrazines. I. The Syntheses of 2,3-Dihydroxypyrazines and Their Derivatives", Journal of Organic Chemistry, vol. 37(2):221-225, 1972.
Fukiage et al., "Involvement of Phosphorylation of Myosin Phosphatase by ROCK in Trabecular Meshwork and Ciliary Muscle Contraction", Biochemical and Biophysical Research Communications, vol. 288:296-300, 2001.
Honjo et al., "Effects of Protein Kinase Inhibitor, HA1077, on Intraocular Pressure and Outflow Facility in Rabbit Eyes", Archives of Ophthalmology, vol. 119:1171-1178, 2001.
Honjo et al., "Effects of Rho-Associated Protein Kinase Inhibitor Y-27632 on Intraocular Pressure and Outflow Facility", IOVS, vol. 42:137-144, 2001.
Ishizaki et al., "Pharmacological Properties of Y-27632, a Specific Inhibitor of Rho-Associated Kinases", Molecular Pharmacology, vol. 57:976-983, 2000.
Loge et al., "Rho-kinase Inhibitors: Pharmacomodulations on the Lead Compound Y-32885", Journal of Enzyme Inhibition and Medicinal Chemistry, vol. 17:381-390, 2002.
Loge et al., "Synthesis and Pharmacological Study of Rho-Kinase Inhibitors: Pharmacomodulations on the Lead Compound Fasudil", Journal of Enzyme Inhibition and Medicinal Chemistry, vol. 18:127-138, 2003.
Rao et al., "Modulation of Aqueous Humor Outflow Facility by the Rho Kinase-Specific Inhibitor Y-27632", IOVS, vol. 42:1029-1037, 2001.
Sasaki et al., "Novel and Specific Rho-Kinase Inhibitor, H1152P, Directed Against the Rho-Kinase Involved Pathway", Cell Biology Molecular Letters, vol. 6(2B):506, 2001.
Sasaki et al., "The Novel and Specific Rho-kinase Inhibitor (S)-(+)-2-methyl-1-[(4-methyl-5-isoquinoline)sulfonyl]-homopiperazine as a Probing Molecule for Rho-kinase-involved Pathway", Pharmacology and Therapeutics, vol. 93:225-232, 2002.

(Continued)

*Primary Examiner*—Frederick Krass
*Assistant Examiner*—Adam Milligan
(74) *Attorney, Agent, or Firm*—Mark E. Flanigan

(57) ABSTRACT

Methods for using 6-aminoimidazo[1,2-b]pyridazine analogs are disclosed herein to treat rho kinase-mediated diseases or rho kinase-mediated conditions, including controlling intraocular pressure and treating glaucoma, are disclosed. Ophthalmic pharmaceutical compositions useful in the treatment of eye diseases such as glaucoma, and additionally useful for controlling intraocular pressure, the compositions comprising an effective amount of 6-aminoimidazo[1,2-b] pyridazine analogs, are disclosed herein.

7 Claims, No Drawings

OTHER PUBLICATIONS

Sato et al., "Studies on Pyrazines. Part 33. Synthesis of 2,3-Diaminopyrazines via [1,2,5]Thiadiazole-[3,4-b] pyrazines", Journal of Chemical Research, vol. 7:250-251, 1997.

Sato et al., "Studies on Pyrazines; Part 30: Synthesis of Aminopyrazines from Azidopyrazines and Azidopyrazines", Synthesis, vol. 9:931-934, 1994.

Sato et al., "Studies on Pyrazines 3. A Facile Synthetic Method for 2,3-Diaminopyrazines", Journal of Organic Chemistry, vol. 43(2):341-343, 1978.

Sato et al., "Studies on Pyrazines. Part 27. A New Deoxidative Nucleophilic Substitution of Pyrazine N-Oxides; Synthesis of Azidopyrazines with Trimethylsilyl Azide", Journal of the Chemical Society Perkin Trans., vol. 7:885-888, 1994.

Satoh et al., "Pharmacological Profile of Hydroxy Fasudil as a Selective Rho Kinase Inhibitor on Ischemic Brain Damage", Life Sciences, vol. 69:1441-1453, 2001.

Sharif et al., "Pharmacological and Molecular Biological (RT-PCR) Characterization of Functional TP Prostanoid Receptors in Immortalized Human Non-Pigmented Ciliary Epithelial Cells", J. Ocular Pharmacology and Therapeutics, vol. 18(2):141-162, 2002.

Sharif et al., "Cloned Human EP Prostanoid Receptor Pharmacology Characterized Using Radioligand Binding Techniques", Journal of Pharmacy and Pharmacology, vol. 54:539-547, 2002.

Sharif et al., "Pharmacology of [3H]Prostaglandin E1/[3H]Prostaglandin E2 and [3H]Prostaglandin F2a Binding to EP3 and FP Prostaglandin Receptor Binding Sites in Bovine Corpus Luteum: Characterization and Correlation with Functional Data", Journal of Pharmacology and Experimental Therapeutics, vol. 286:1094-1102, 1998.

Sharif et al., "Affinities, Selectivities, Potencies and Intrinsic Activities of Natural and Synthetic Prostanoids Using Endogenous Receptors: Focus on DP Class Prostanoids", Journal of Pharmacology and Experimental Therapeutics, vol. 293:321-328, 2000.

Takami et al., "Design and Synthesis of Rho Kinase Inhibitors (I)", Bioorganic and Medicinal Chemistry, vol. 12:2115-2137, 2004.

Thieme et al., "Mediation of Calcium-Independent Contraction in Trabecular Meshwork Through Protein Kinase C and Rho-A", IOVS, vol. 41:4240-4246, 2000.

Tian et al., "Effects of Topical -7 on Outflow Facility, Intraocular Pressure and Corneal Thickness in Monkeys", Archives of Ophthalmology, vol. 122:1171-1177, 2004.

Uehata et al., "Calcium Sensitization of Smooth Muscle Mediated by Rho-associated Protein Kinase in Hypertension", Nature, vol. 389:990-994, 1997.

Waki et al., "Reduction of Intraocular Pressure by Topical Administration of an Inhibitor of the Rho-associated Protein Kinase", Current Eye Research, vol. 22(6):470-474, 2001.

Wettschureck et al., "Rho/Rho-kinase Mediated Signaling in Physiology and Pathophysiology", Journal of Molecular Medicine, vol. 80:629-638, 2002.

US 6,503,924, 01/2003, Azuma et al. (withdrawn)

* cited by examiner

6-AMINOIMIDAZO[1,2-B]PYRIDAZINE ANALOGS AS RHO KINASE INHIBITORS FOR THE TREATMENT OF RHO KINASE-MEDIATED DISEASES AND CONDITIONS

CROSS-REFERENCE TO RELATED APPLICATION

This application claims priority under 35 U.S.C. §119 to U.S. Provisional Patent Application No. 60/871,422, filed Dec. 21, 2006, the entire contents of which are incorporated herein by reference.

TECHNICAL FIELD OF THE INVENTION

The present invention is directed to 6-aminoimidazo[1,2-b]pyridazine analogs and the use of such compounds to treat rho kinase-mediated diseases and conditions. The invention is particularly directed to uses of such compounds for lowering and/or controlling normal or elevated intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated, but no apparent loss of visual function has occurred; such patients are considered to be at high risk for the eventual development of the visual loss associated with glaucoma. Some patients with glaucomatous field loss have relatively low intraocular pressure. These normotension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated.

Drug therapies that have proven to be effective for the reduction of intraocular pressure include both agents that decrease aqueous humor production and agents that increase the outflow facility. Such therapies are in general administered by one of two possible routes, topically (direct application to the eye) or orally. However, pharmaceutical ocular anti-hypertension approaches have exhibited various undesirable side effects. For example, miotics such as pilocarpine can cause blurring of vision, headaches, and other negative visual side effects. Systemically administered carbonic anhydrase inhibitors can also cause nausea, dyspepsia, fatigue, and metabolic acidosis. Certain prostaglandins cause hyperemia, ocular itching, and darkening of eyelashes and periorbital tissues. Further, certain beta-blockers have increasingly become associated with serious pulmonary side-effects attributable to their effects on beta-2 receptors in pulmonary tissue. Sympathomimetics cause tachycardia, arrhythmia and hypertension. Such negative side-effects may lead to decreased patient compliance or to termination of therapy such that normal vision continues to deteriorate. Additionally, there are individuals who simply do not respond well when treated with certain existing glaucoma therapies. There is, therefore, a need for other therapeutic agents that control IOP.

The small rho GTPases are involved in many cellular functions including cell adhesion, cell motility, cell migration, and cell contraction. One of the main effectors of the cellular functions associated with this class of proteins is rho-associated coiled-coil-forming protein kinase (rho kinase) which appears to have an important role in the regulation of force and velocity of smooth muscle contraction, tumor cell metastasis and inhibition of neurite outgrowth. Rho kinase is a serine/threonine protein kinase that exists in two isoforms: ROCK1 (ROKβ) and ROCK2 (ROKα) [Wettschureck et al., Journal of Molecular Medicine, Vol. 80:629-638, 2002; Uehata et al., Nature, Vol. 389:990-994, 1997; Ishizaki et al., Molecular Pharmacology, Vol. 57:976-983, 2000; Loge et al., Journal of Enzyme Inhibition and Medicinal Chemistry, Vol. 17:381-390, 2002].

It has been found that certain inhibitors of rho kinase effectively lower and control normal and elevated IOP [Honjo et al., Investigative Ophthalmology and Visual Science, Vol. 42:137-144, 2001; Honjo et al., Archives of Ophthalmology, Vol. 119:1171-1178, 2001; Rao et. al., Investigative Ophthalmology and Visual Science, Vol. 42:1029-1037, 2001; Waki, Current Eye Research, Vol. 22:470-474, 2001; Tian et al., Archives of Ophthalmology, Vol. 122:1171-1177, 2004]. Rho kinase inhibitors such as H-7 and Y-27632 inhibit ciliary muscle contraction and trabecular cell contraction, effects that may be related to the ocular hypotensive effect of this class of compounds [Thieme et al., Investigative Ophthalmology and Visual Science, Vol. 41:4240-4246, 2000; Fukiage et al., Biochemical and Biophysical Research Communications, Vol. 288:296-300, 2001].

Compounds that act as rho kinase inhibitors are well known and have shown a variety of utilities. Pyridine, indazole, and isoquinoline compounds that have rho kinase activity are described by Takami et al., Biorganic and Medicinal Chemistry, Vol. 12:2115-2137, 2004. U.S. Pat. Nos. 6,218,410 and 6,451,825 disclose the use of rho kinase inhibitors for the treatment of hypertension, retinopathy, cerebrovascular contraction, asthma, inflammation, angina pectoris, peripheral circulation disorder, immature birth, osteoporosis, cancer, inflammation, immune disease, autoimmune disease and the like. U.S. Pat. No. 6,794,398 describes the use of a compound with rho kinase activity for the prevention or treatment of liver diseases. U.S. Pat. No. 6,720,341 describes the use of compounds with rho kinase activity for the treatment of kidney disease. WO 99/23113 describes the use of rho kinase inhibitors to block the inhibition of neurite outgrowth. WO 03/062227 describes 2,4-diaminopyrimidine derivatives as rho kinase inhibitors. WO 03/059913 describes bicyclic 4-aminopyrimidine analogs as rho kinase inhibitors. WO 02/100833 describes heterocyclic compounds as rho kinase inhibitors. WO 01/68607 describes amide derivatives as rho kinase inhibitors. WO 04/024717 describes amino isoquinoline derivatives as rho kinase inhibitors. WO 04/009555 describes 5-substituted isoquinoline derivatives as rho kinase inhibitors useful for treating glaucoma, bronchial asthma and chronic obstructive pulmonary disease. EP1034793 describes the use of rho kinase inhibitors for the treatment of glaucoma.

U.S. Pat. Nos. 6,503,924, 6,649,625, and 6,673,812 disclose the use of amide derivatives that are rho kinase inhibitors for the treatment of glaucoma. U.S. Pat. Nos. 5,798,380 and 6,110,912 disclose a method for treating glaucoma using serine/threonine kinase inhibitors. U.S. Pat. No. 6,586,425 describes a method for treating glaucoma using serine/threonine kinase inhibitors. U.S. Patent Application Publication No. 2002/0045585 describes a method for treating glaucoma using serine/threonine kinase inhibitors.

The following references disclose the activity of isoquinoline sulfonamide analogs as rho kinase inhibitors: Sasaki, Cellular Biology Molecular Letters, Vol. 6:506, 2001; Satoh et al., Life Sciences, Vol. 69:1441-1453, 2001; Sasaki, Pharmacology and Therapeutics, Vol. 93:225-232, 2002; Loge et al., Journal of Enzyme Inhibition and Medicinal Chemistry, Vol. 18:127-138, 2003. The use of certain isoquinolinesulfonyl compounds for the treatment of glaucoma has been disclosed in U.S. Pat. Nos. 6,271,224 and 6,403,590. Also, WO 04/000318 describes the use of amino-substituted monocycles as AKT-1 kinase modulators.

Several publications have described the synthesis of pyrazines. WO 04/084824 describes the preparation of biaryl substituted 6-membered heterocycles for use as sodium channel blockers. WO 04/085409 describes the preparation of libraries of compounds, including pyrazines, that are capable of binding to the active site of protein kinase. Other publications involving methods of pyrazine synthesis include: Sato et al., Journal of Chemical Research, Vol. 7:250-1, 1997; Sato et al., Synthesis, Vol. 9:931-4, 1994; Sato, Journal of the Chemical Society, Vol. 7:885-8, 1994; Sato, Journal of Organic Chemistry, Vol. 43(2):341-3, 1978; Adachi et al., Journal of Organic Chemistry, Vol. 37(2):221-5, 1972.

SUMMARY OF THE INVENTION

The present invention is directed 6-aminoimidazo[1,2-b]pyridazine analogs described herein, and their use to treat rho kinase-mediated diseases and conditions.

The subject compounds of Formula I described below can be used to lower and/or control IOP associated with normal-tension glaucoma, ocular hypertension, and glaucoma in warm blooded animals, including man. In certain embodiments, when used to treat normal-tension glaucoma or ocular hypertension, the compounds may be formulated in pharmaceutically acceptable compositions suitable for topical delivery to the eye.

Another embodiment of the present invention contemplates an ophthalmic pharmaceutical composition useful in the treatment of glaucoma and control of intraocular pressure, comprising an effective amount of a compound according to Formula I.

Another embodiment of the present invention comprises a method of controlling intraocular pressure comprising administering a therapeutically effective amount of an ophthalmic pharmaceutical composition useful in the treatment of glaucoma and control of intraocular pressure to a human or other mammal, where the composition comprises an effective amount of a compound according to Formula I.

Yet other embodiments of the present invention comprise methods of treating rho kinase-mediated diseases or rho kinase-mediated conditions, which comprise administering to a human or other mammal a therapeutically effective amount of a compound or compounds according to Formula I.

As used herein, the term "rho kinase-mediated disease" or "rho kinase-mediated condition," means any disease or other deleterious condition in which rho kinase is known to play a role. Such conditions include, without limitation, hypertension, glaucoma, retinopathy, cerebrovascular contraction, ocular hypertension, normal-tension glaucoma, chronic obstructive pulmonary disease, asthma, inflammation, angina pectoris, peripheral circulation disorder, immature birth, osteoporosis, cancer, inflammation, immune disease, autoimmune disease.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention when considered in connection with any accompanying examples. However, examples provided herein are intended to help illustrate the invention or assist with developing an understanding of the invention, and are not intended to be definitions of the invention's scope.

DETAILED DESCRIPTION OF THE INVENTION

Embodiments of the present invention provide compounds useful for treating rho kinase-mediated diseases and conditions and/or lowering and controlling normal or elevated intraocular pressure (IOP) and/or treating glaucoma. Such compounds may be represented by the following Formula I:

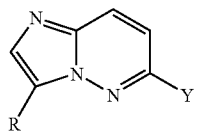

Formula I where:
R=heteroaryl, $C_1$-$C_{12}$ branched or straight chain, or cyclic alkyl, alkenyl, alkynyl optionally substituted by $NR^2R^3$, OH, $OR^4$, aryl, heteroaryl, or heterocyclyl, aryl, heteroaryl, or heterocyclyl;
$R^2$, $R^3$ independently=H, $C_1$-$C_6$ alkyl optionally substituted by $NR^5R^6$, OH, $OR^4$, aryl, heteroaryl, or heterocyclyl;
$R^2$ and $R^3$ together can form a heterocyclic ring;
$R^4$=$C_1$-$C_6$ alkyl, aryl, heteroaryl;
$R^5$, $R^6$ independently=H, $C_1$-$C_6$ alkyl optionally substituted by OH, $OR^4$, aryl, or heteroaryl;
$R^5$ and $R^6$ together can form a heterocyclic ring;
Y=$NR^7R^8$; $NHR^7$;
$R^7$, $R^8$ independently=H $NR^7R^8$, $NR^7$; $C_1$-$C_6$ alkyl optionally substituted by —$(CH_2)_n NR^4R^5$, —$(CH_2)_n OH$, —$(CH_2)_n OR^6$, —$(CH_2)_n$aryl, or —$(CH_2)_n$heteroaryl; or $C_3$-$C_8$ cyclic alkyl optionally substituted by —$(CH_2)_n$ $NR^5R^6$, —$(CH_2)_n OH$, —$(CH_2)_n OR^4$, —$(CH_2)_n$aryl, or —$(CH_2)_n$heteroaryl; or $R^7$ and $R^8$ together can form a heterocylic ring optionally substituted by —$(CH_2)_n$ $NR^5R^6$, —$(CH_2)_n OH$, —$(CH_2)_n OR^4$, —$(CH_2)_n$aryl, or —$(CH_2)_n$heteroaryl; and
n=0-4.

The preferred compounds are those of Formula I in which:
R=heteroaryl;
$R^7$, $R^8$ independently=H; $C_1$-$C_4$ alkyl optionally substituted by —$(CH_2)_n NR^5R^6$, —$(CH_2)_n OH$, —$(CH_2)_n OR^4$; or $R^7$ and $R^8$ together can form a heterocyclic ring;
$R^4$,$R^5$ independently=H; $C_1$-$C_6$ alkyl optionally substituted by OH, $OR^4$, aryl, or heteroaryl; and
n=0-2

The most preferred compounds are those of Formula I in which:

R =

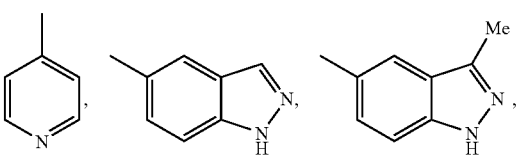

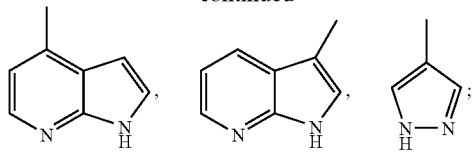

Y=NHR⁷, R⁷=H; $C_1$-$C_4$ alkyl optionally substituted by —$(CH_2)_nNR^5R^6$, —$(CH_2)_nOH$, —$(CH_2)_nOR^4$;

or

Y=NR⁷R⁸ where R⁷ and R⁸ together can form a heterocylic ring optionally substituted by —$(CH_2)_nNR^5R^6$, —$(CH_2)_nOH$; and R⁵, R⁶ independently=H; $C_1$-$C_6$ alkyl optionally substituted by OH, OR⁴, aryl, or heteroaryl.

Other compounds that are particularly preferred are:
3-(1H-Indazol-5-yl)-6-piperazin-1-yl-imidazo[1,2-b]pyridazine dihydrochloride, 3-(3-Methyl-1H-indazol-5-yl)-6-piperazin-1-yl-imidazo[1,2-b]pyridazine, [3-(3-methyl-1H-indazol-5-yl)-imidazo[1,2-b]pyridazine-6-yl]-piperidin-3-yl-amine trihydrochloride, 6-(1,4-Diazepan-1-yl)-3-pyridin-4-yl-imidazo[1,2-b]pyridazine hydrochloride, and 3 -(3-Methyl-1H-indazol-5-yl)-6-perhydro-1,4-diazepin-1-yl-imidazo[1,2-b]pyridazine trihydrochloride.

It is recognized that compounds of Formula I can contain one or more chiral centers. This invention contemplates all enantiomers, diastereomers, and mixtures of Formulas I thereof.

Furthermore, certain embodiments of the present invention comprise pharmaceutically acceptable salts of compounds according to Formula I. Pharmaceutically acceptable salts comprise, but are not limited to, soluble or dispersible forms of compounds according to Formula I that are suitable for treatment of disease without undue undesirable effects such as allergic reactions or toxicity. Representative pharmaceutically acceptable salts include, but are not limited to, acid addition salts such as acetate, citrate, benzoate, lactate, or phosphate and basic addition salts such as lithium, sodium, potassium, or aluminum.

The term "aryl" as used herein refers to a monocyclic, bicyclic or tricyclic ring system having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having three to fourteen ring members in which one or more ring members is a heteroatom, wherein each ring in the system contains 3 to 7 ring members.

The term "heteroaryl" refers to monocyclic, bicyclic or tricyclic ring systems having three to fourteen ring members wherein at least one ring in the system is aromatic, at least one ring in the system contains one or more heteroatoms, and wherein each ring in the system contains 3 to 7 ring members.

In the above definitions, the total number of carbon atoms in a substituent group is indicated by the $C_{i-j}$ prefix, where the numbers i and j define the number of carbon atoms; this definition includes straight chain, branched chain, and cyclic alkyl or (cyclic alkyl)alkyl groups.

It is important to recognize that a substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

SYNTHESIS EXAMPLES

Compounds according to Formula I can be prepared by using synthetic procedures described herein, several examples of which are provided below. Unless otherwise noted, reagents and solvents were used as received from commercial suppliers. Purifications using the notation 'column' were carried out on an automated Combiflash unit consisting of a gradient mixing system, Foxy 200 fraction collector and a UV/visible detector. Proton and carbon nuclear magnetic resonance spectra were obtained on a Bruker AC 300 or a Bruker AV 300 spectrometer at 300 MHz for proton and 75 MHz for carbon, or on a Bruker AMX 500 spectrometer at 500 MHz for proton and 125 MHz for carbon. Spectra are given in ppm (δ) and coupling constants, J, are reported in Hertz. Tetramethylsilane was used as an internal standard for proton spectra and the solvent peak was used as the reference peak for carbon spectra. Mass spectra were obtained on a Finnigan LCQ Duo LCMS ion trap electrospray ionization (ESI) mass spectrometer. Thin-layer chromatography (TLC) was performed using Analtech silica gel plates and visualized by ultraviolet (UV) light unless otherwise stated. HPLC analyses were obtained using a (Luna) C18(2) column (250× 4.6 mm, Phenonemex) or Synergi Hydro-RP column (250× 4.6 mm, Phenonemex) with UV detection at 254 nm using a standard solvent gradient program (Method A). Semi-prep HPLC was performed using a (Luna) C18(2) column (250× 21.2 mm, 10 u, Phenonemex) and Method A with a flow of 18 mL/min. The eluent was concentrated and partitioned between an organic solvent and saturated sodium carbonate solution. Concentration of the organic layer provided the purified product as a free-base. Liquid chromatography-mass spectrometry was obtained on a Varian 1200L single quadrapole mass spectrometer using ESI and a Luna C18(2) column (50×4.6 mm, Phenonemex) with UV detection at 254 nm using a standard solvent gradient program (Method B).

| Method A: | | | | Method B: | | | |
|---|---|---|---|---|---|---|---|
| Time (min) | Flow (mL/min) | % A | % B | Time (min) | Flow (mL/min) | % A | % B |
| 0.0 | 1.0 | 98.0 | 2.0 | 0.0 | 2.5 | 90.0 | 10.0 |
| 25 | 1.0 | 10.0 | 90.0 | 4 | 2.5 | 0.0 | 100.0 |
| 30 | 1.0 | 10.0 | 90.0 | 6 | 2.5 | 0.0 | 100.0 |
| 35 | 1.0 | 98.0 | 2.0 | 7 | 2.5 | 90.0 | 10.0 |

A = 100% Water with 0.025% or 0.05% v/v Trifluoroacetic Acid
B = 100% Acetonitrile, 0.025% or 0.05% v/v Trifluoroacetic Acid General Scheme 1

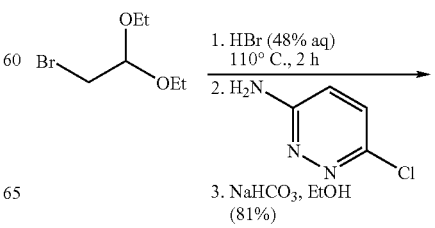

-continued

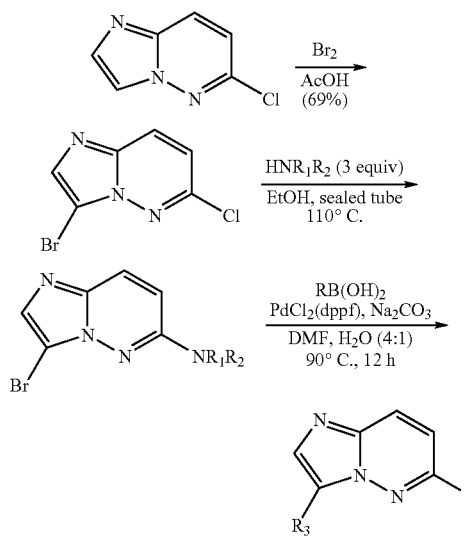

General Scheme 2

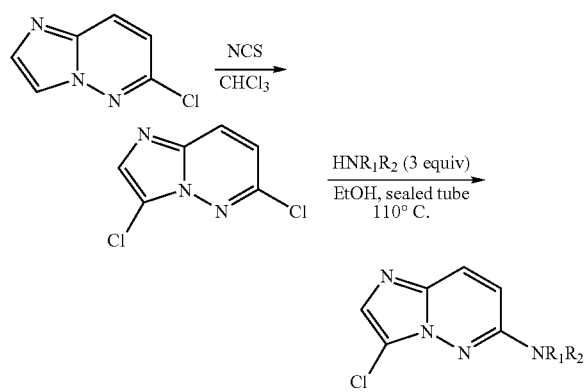

General Scheme 3

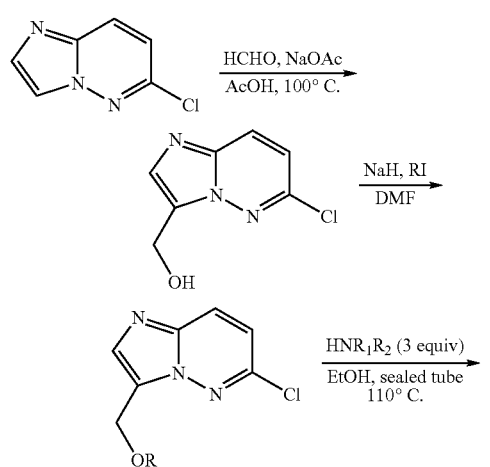

-continued

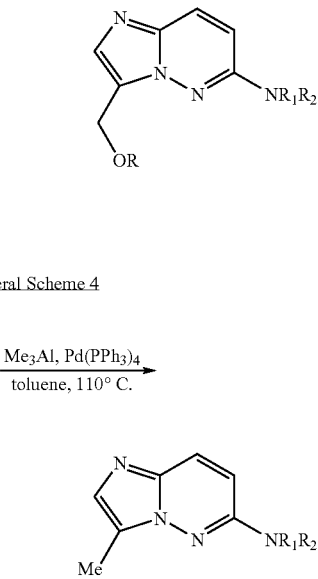

General Scheme 4

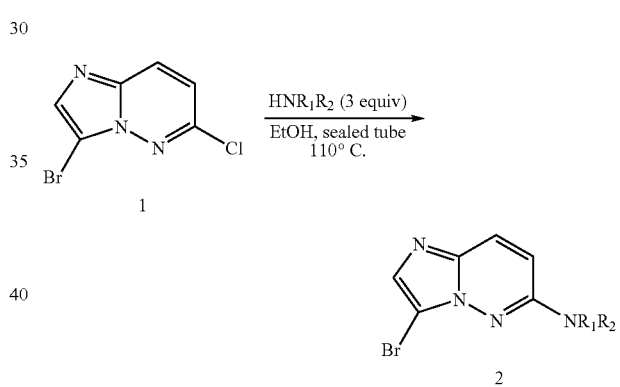

General Procedure 1: Preparation of Bromoimidazoaminopyridazine 2 From Bromoimidazochloropyridazine 1.

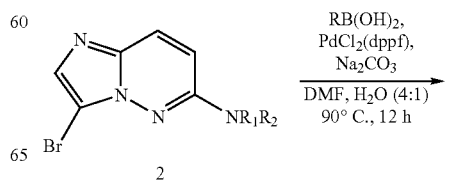

A mixture of 3-bromo-6-chloroimidazo[1,2-b]pyridazine 1[1] (2 mmol) and amine (6 mmol) was heated at 110° C. in a sealed tube for 15 h. The reaction mixture was concentrated and purified by column chromatography (12 g ISCO column eluting with methylene chloride and a methanol/ammonia mixture (10:1); gradient 100% methylene chloride to 80% methylene chloride over 30 min at 25 mL/min) to provide the desired product.

General Procedure 2: Preparation of Imidazopyridazine 3 from Bromoimidazoaminopyridazine 2.

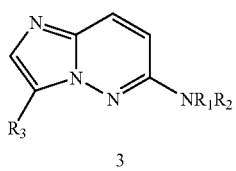

Bromoimidazoaminopyridazine 2 (1 mmol), boronic acid (1.5 mmol, 1.5 eq.) and Na$_2$CO$_3$ (316 mg, 3 mmol, 3 eq.) were stirred in DMF (4 mL) and water (1 mL) and the resulting mixture was degassed with a nitrogen stream as the temperature was increased to 100° C. After degassing at this temperature for 10 min, Pd(dppf)Cl$_2$ (82 mg, 0.1 mmol, 0.1 equiv) was added and the reaction was stirred at 100° C. under a nitrogen atmosphere for 18 h. Upon cooling the mixture was poured into water (50 mL) and stirred for 10 min. The mixture was extracted with ethyl acetate and the combined organic extracts washed with 5% Lithium Chloride (5x), dried over sodium sulfate and concentrated to provide the crude product 3. Purification by column chromatography (12 g ISCO column eluting with methylene chloride and a methanol/ammonia mixture (10:1); gradient 100% methylene chloride to 70% methylene chloride over 30 min at 25 mL/min) provided the pure desired product 3.

General Procedure 3: Preparation of Chloroimidazoaminopyridazine 6 from Imidazochloropyridazine 4.

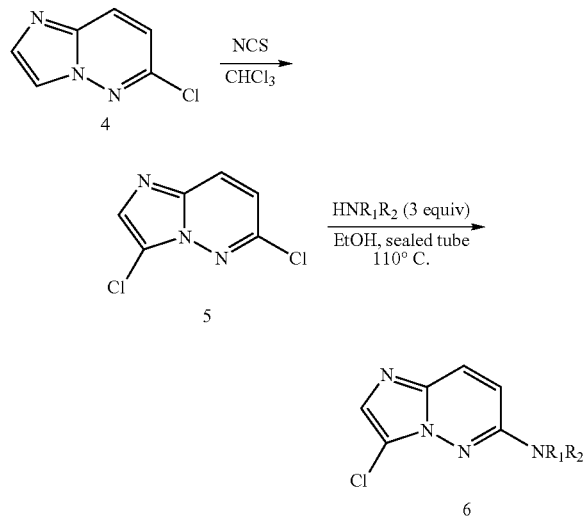

6-Chloroimidazo[1,2-b]pyridazine 4$^1$ (6.53 mmol) was dissolved in chloroform (12 mL) and N-chlorosuccinimide (6.53 mmol) added under N$_2$. After stirring for 16 h, the mixture was partitioned between saturated sodium hydrogensulfate solution (25 mL) and chloroform (12 mL). The organic layer was removed, washed with water (2x), dried and concentrated to provide 3,6-dichloroimidazo[1,2-b]pyridazine 5 (1.05 g, 85%) as an orange solid; $^1$H NMR (500 MHz, CDCl$_3$) δ 7.92 (d, J=9.5 Hz, 1H), 7.74 (s, 1H), 7.12 (d, J=9.5 Hz, 1H). 3,6-Dichloroimidazo[1,2-b]pyridazine 5 (150 mg, 0.8 mmol) and the desired amine (1 mL) were heated in a sealed tube for 16 hr at 120° C. Upon cooling the reaction mixture was concentrated and purified by column chromatography (12 g ISCO column eluting with methylene chloride and a methanol/ammonia mixture (10:1); gradient 100% methylene chloride to 80% methylene chloride over 30 min at 25 mL/min) to provide the desired product 6.

General Procedure 4: Preparation of Alkoxyimidazoaminopyridazine 9 from Imidazochloropyridazine 7.

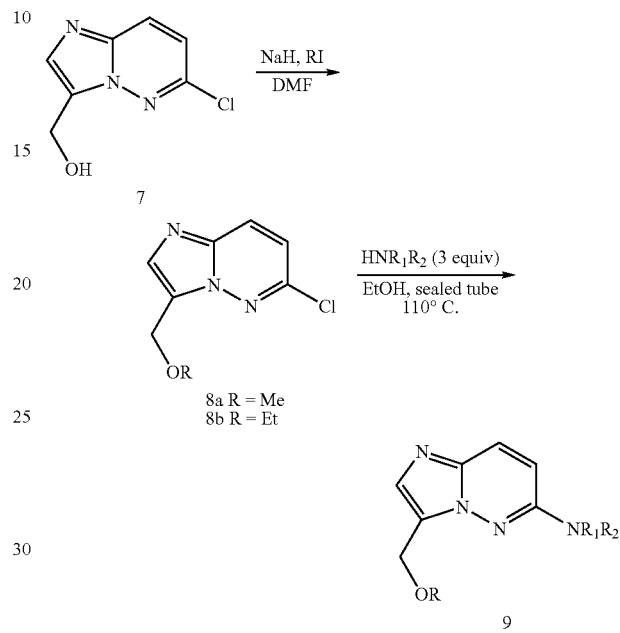

Step A: (6-Chloroimidazo[1,2-b]pyridazin-3-yl)methanol 7$^2$ (1 mmol) and the alkyl iodide (1.1 mmol) were dissolved in dry DMF (2 mL) and sodium hydride (60% disp, 1.1 mmol) added. After 2 h the mixture was poured into water and extracted (2x) with ethyl acetate. The combined organic layers were washed with 5% lithium chloride solution (5x), dried, concentrated and the residue purified by column chromatography (12 g ISCO column eluting with methylene chloride and a methanol/ammonia mixture (10:1); gradient 100% methylene chloride to 80% methylene chloride over 30 min at 25 mL/min) to provide the desired product 8.

8a 6-Chloro-3-(methoxymethyl)imidazo[1,2-b]pyridazine was obtained as a yellow oil (100 mg, 51%); R$_f$=0.90 (CH$_2$Cl$_2$/MeOH/NH$_4$OH, 160:18:2); $^1$H NMR (500 MHz, CD$_3$OD) δ 8.05 (d, J=9.5 Hz, 1H), 7.81 (s, 1H), 7.34 (d, J=9.5 Hz, 1H), 4.85 (s, 2H), 3.41 (s, 3H).

8b 6-Chloro-3-(ethoxymethyl)imidazo[1,2-b]pyridazine was obtained as a yellow oil (111 mg, 53%); R$_f$=0.90 (CH$_2$Cl$_2$/MeOH/NH$_4$OH, 160:18:2); $^1$H NMR (500 MHz, CD$_3$OD) δ 8.01 (d, J=9.5 Hz, 1H), 7.80 (s, 1H), 7.34 (d, J=9.5 Hz, 1H), 4.87 (s, 2H), 3.63 (quart, J=7.0 Hz, 2H), 1.21 (t, J=7.0 Hz, 3H).

Step B: Compound 8a or 8b (0.58 mmol) and HNR$_1$R$_2$ (500 mg) were heated at 120° C. in a sealed tube for 15 h. The reaction mixture was concentrated and purified by column chromatography (12 g ISCO column eluting with methylene chloride and a methanol/ammonia mixture (10:1); gradient 100% methylene chloride to 80% methylene chloride over 30 min at 25 mL/min) to provide the desired product 9.

General Procedure 5: Preparation of Methylimidazoaminopyridazine 10 from Bromoimidazoaminopyridazine 2.

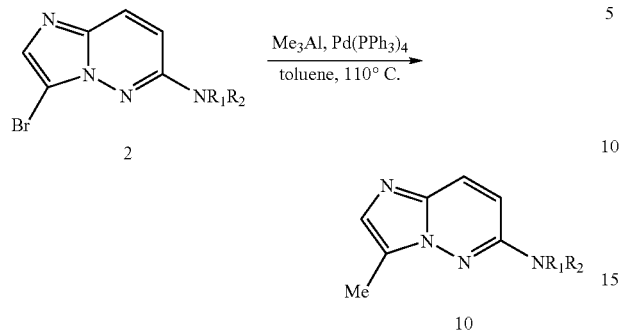

A mixture of aryl bromide 2 (0.61 mmol) and trimethylaluminum (2M in toluene, 1.85 mmol) in anhydrous THF (4 mL) were degassed with a stream of nitrogen as the temperature was increased to 60° C. Tetrakistriphenylphoshinepalladium (70 mg, 0.61 mmol) was added and the mixture heated at 60° C. for 16 h under an inert atmosphere. The reaction mixture was concentrated and purified by column chromatography (12 g ISCO column eluting with methylene chloride and a methanol/ammonia mixture (10:1); gradient 100% methylene chloride to 70% methylene chloride over 30 min at 25 mL/min) to provide the desired product 10.

General Procedure 6: Preparation of Acetlyeneoimidazoaminopyridazine 11 from Bromoimidazoaminopyridazine 2.

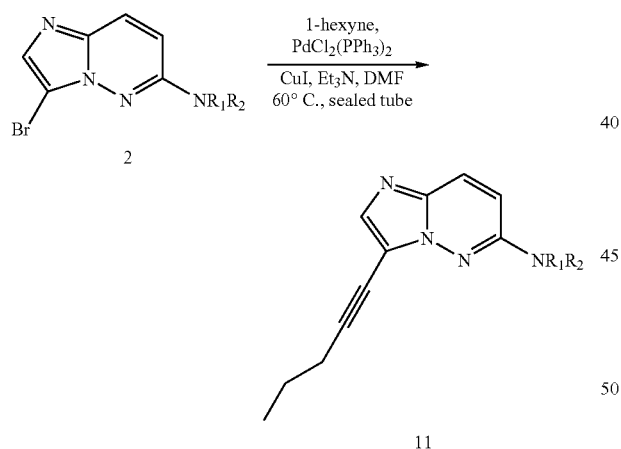

Aryl bromide 2 (0.38 mmol) was dissolved in dry DMF (2 mL) and degassed with a stream of nitrogen. 1-Hexyne (47 mg, 0.57 mmol), dichlorobistriphenylphosphine palladium (26 mg, 0.038 mmol), copper (I) iodide (7 mg, 0.038 mmol) and triethylamine (115 mg, 1.14 mmol) were added and the mixture heated in a sealed tube at 60° C. overnight. Upon cooling the mixture was poured into water and extracted (2×) with ethyl acetate. The combined organic layers were washed with 5% lithium chloride solution (5×), dried, concentrated and the residue purified by column chromatography (12 g ISCO column eluting with methylene chloride and a methanol/ammonia mixture (10:1); gradient 100% methylene chloride to 80% methylene chloride over 30 min at 25 mL/min) to provide the desired product 11.

Example 1

3-(4-Methoxyphenyl)-N-(pyridin-2-ylmethyl)imidazo[1,2-b]pyridazin-6-amine

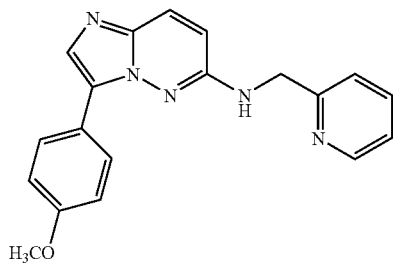

Step A: 3-Bromo-N-(pyridin-2-ylmethyl)imidazo[1,2-b]pyridazin-6-amine

Prepared from 3-bromo-6-chloroimidazo[1,2-b]pyridazine and 2-(aminomethyl)pyridine according to general procedure 1 providing the amino compound (97 mg, 25%) as a white solid; $R_f$=0.80 ($CH_2Cl_2$/MeOH/$NH_4OH$, 160:18:2); $^1$H NMR (500 MHz, $CD_3OD$) δ 8.52-8.51 (m, 1H), 7.83-7.79 (m, 1H), 7.63 (d, J=9.7 Hz, 1H), 7.59 (d, J=7.9 Hz, 1H), 7.41 (s, 1H), 7.33-7.31 (m, 1H), 6.84 (d, J=9.7 Hz, 1H), 4.70 (s, 2H); ES-MS: (M+H)=304, 306 m/z.

Step B: Prepared from the product of step A and 4-methoxyphenylboronic acid according to general procedure 2, providing the title compound (45 mg, 83%) as a grey solid; $^1$H NMR (300 MHz, $CDCl_3$) δ 8.61 (d, J=4.4 Hz, 1H), 7.95 (d, J=8.9 Hz, 2H), 7.76-7.66 (m, 3H), 7.37 (d, J=7.8 Hz, 1H), 7.25-7.20 (m, 1H, partially masked by solvent), 6.99 (d, J=8.9 Hz, 2H), 6.58 (d, J=9.5 Hz, 1H), 5.77 (br, 1H), 4.74 (d, J=4.8 Hz, 2H), 3.88 (s, 3H); $^{13}$C NMR (125 MHz, $CDCl_3$) δ 158.9, 156.8, 152.6, 149.0, 136.6, 131.2, 128.3, 128.2, 128.0, 126.2, 122.3, 122.2, 122.1, 113.9, 110.9, 55.3, 44.8; HPLC $t_R$=7.76 min (Luna), 95.0%; ES-MS: (M+H)=332 m/z.

Example 2

3-(2-Methoxyphenyl)-N-(pyridin-2-ylmethyl)imidazo[1,2-b]pyridazin-6-amine fumarate

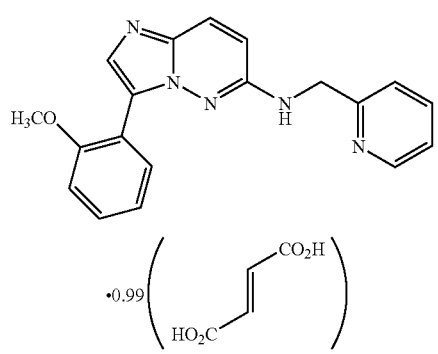

Prepared from the product of step A (example 1) and 2-methoxphenylboronic acid according to general procedure 2. Treatment with fumaric acid (0.99 equiv) in methanol (1 mL) provided the fumarate salt of the title compound (37 mg, 50%) as a white solid: $^1$H NMR (500 MHz, CD$_3$OD) δ 8.52 (d, J=4.9 Hz, 1H), 7.78-7.75 (m, 3H), 7.64 (dd, J=7.7, 1.7 Hz, 1H), 7.43 (d, J=7.9 Hz, 1H), 7.36-7.30 (m, 2H), 7.08 (d, J=8.3 Hz, 1H), 6.94 (d, J=9.9 Hz, 1H), 6.88 (td, J=7.6, 2.0 Hz, 1H), 6.76 (s, 2H), 4.61 (s, 2H), 3.74 (s, 3H); $^{13}$C NMR (75 MHz, CD$_3$OD) δ 168.7, 159.9, 158.3, 154.9, 149.6, 138.7, 136.8, 135.4, 130.8, 130.6, 130.5, 126.2, 125.1, 123.6, 123.0, 121.2, 118.2, 114.8, 112.1, 56.0, 47.7; HPLC t$_R$=7.56 min (Luna), 98.7%; ES-MS: (M+H)=332 m/z.

Example 3

4-(3-(1H-Pyrazol-4-yl)imidazo[1,2-b]pyridazin-6-yl) morpholine

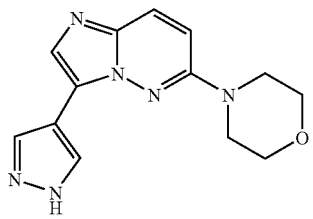

Step A:
4-(3-Bromoimidazo[1,2-b]pyridazin-6-yl)morpholine

Prepared from 3-bromo-6-chloroimidazo[1,2-b]pyridazine and morpholine according to general procedure 1 providing the amino compound (235 mg, 85%) as a yellow solid: R$_f$=0.79 (CH$_2$Cl$_2$/MeOH/NH$_4$OH, 160:18:2); $^1$H NMR (500 MHz, CDCl$_3$) δ 7.70 (d, J=9.9 Hz, 1H), 7.53 (s, 1H), 6.81 (d, J=9.9 Hz, 1H), 3.86 (t, J=5.0 Hz, 4H), 3.55 (t, J=4.8 Hz, 4H); ES-MS: (M+H)=283, 285 m/z.

Step B: 4-(4,4,5,5-Tetramethyl-1,3,2-dioxaborolan-2-yl)-1-((2-(trimethylsilyl)ethoxy)methyl)-1H-pyrazole 4-(4,4,5,5-Tetramethyl-1,3,2-dioxaborolan-2-yl)-1H-pyrazole (348 mg, 1.8 mmol) was dissolved in DMF (5 mL) and sodium hydride (60% dispersion, 86 mg, 2.15 mmol) added and the mixture heated to 60° C. for 5 min. Upon cooling and stirring for an additional 15 min, trimethylsilylethoxymethyl chloride (358 mg, 2.15 mmol, 381 µL) was added dropwise over 5 min and mixture stirred for 16 h. The reaction mixture was diluted with ethyl acetate (25 mL), washed with 5% lithium chloride (5×), dried over sodium sulfate and concentrated. The residue was purified by column chromatography (40 g ISCO column eluting with hexanes and ethyl acetate; gradient 100% hexanes to 50% hexanes over 30 min at 30 mL/min) to provide the SEM-protected pyrazole (360 mg, 61%) as a colorless oil; $^1$H NMR (500 MHz, CDCl$_3$) δ 7.84 (s, 1H), 7.80 (s, 1H), 5.42 (s, 2H), 3.56-3.53 (t, J=8.3 Hz, 2H), 1.31 (s, 12H), 0.91-0.87 (t, J=8.3 Hz, 2H), −0.03 (s, 9H).

Step C: 4-(3-(1-((2-(Trimethylsilyl)ethoxy)methyl)-1H-pyrazol-4-yl)imidazo[1,2-b]pyridazin-6-yl)morpholine Prepared from the products of step A and step B according to general procedure 2 providing the title compound as a yellow oil (470 mg, >100%) with some impurities present: $^1$H NMR (500 MHz, CDCl$_3$) δ 8.23 (s, 1H), 8.13 (s, 1H), 7.80-7.77 (m,2H), 6.79 (d, J=9.8 Hz, 1H), 5.51 (s, 2H), 3.89 (t, J=4.8 Hz, 4H), 3.62 (t, J=8.4 Hz, 2H), 3.52 (t, J=4.9 Hz, 4H), 0.92 (t, J=8.3 Hz, 2H), −0.02 (s, 9H); ES-MS:(M+H)=401 m/z.

Step D: The product from step C (284 mg, 0.71 mmol) was heated to 60° C. in a mixture of TFA (5 mL) and water (1 mL) for 1 h. Upon cooling the reaction mixture was concentrated and partitioned between ethyl acetate and saturated sodium carbonate solution. The solid that formed at the solvent interface was removed by filtration and dried under vacuum to provide the pure title compound (63 mg, 33%) as a white solid: $^1$H NMR (500 MHz, DMSO-d$_6$) δ 11.02 (s, 1H), 8.40 (s, 1H), 8.17 (s, 1H), 7.89 (d, J=9.9 Hz, 1H), 7.84 (s, 1H), 7.15 (d, J=9.9 Hz, 1H), 3.79 (t, J=3.9 Hz, 4H), 3.52 (t, J=4.3 Hz, 4H); $^{13}$C NMR (125 MHz, DMSO-d$_6$) δ 155.2, 136.1, 135.8, 128.4, 125.8, 125.1, 121.8, 109.2, 108.6, 65.6, 46.0; HPLC t$_R$=13.6 min (Luna), >99%; ES-MS: (M+H)=271 m/z.

Example 4

3-(4-Methylthiophen-2-yl)-N-propylimidazo[1,2-b] pyridazin-6-amine

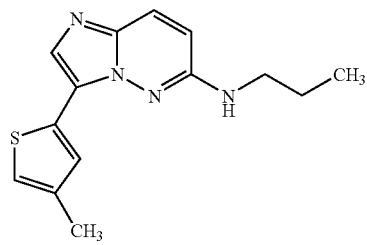

Step A: 3-Bromo-N-propylimidazo[1,2-b]pyridazin-6-amine

Prepared from 3-bromo-6-chloroimidazo[1,2-b]pyridazine and propylamine according to general procedure 1 providing the amino compound (247 mg, 100%) as a yellow solid: R$_f$=0.88 (CH$_2$Cl$_2$/MeOH/NH$_4$OH, 160:18:2); $^1$H NMR (500 MHz, CDCl$_3$) δ 7.57 (d, J=9.6 Hz, 1H), 7.49 (s, 1H), 6.41 (d, J=9.6 Hz, 1H), 4.47 (br, 1H), 3.41-3.37 (m, 2H), 1.70 (sext, J=7.3 Hz, 2H), 1.03 (t, J=7.5 Hz, 3H); ES-MS: (M+H)=255, 257 m/z.

Step B: Prepared from the product of step A and 4-methylthiophene-2-boronic acid according to general procedure 2 providing the title compound (30 mg, 16%) as a brown solid: $^1$H NMR (500 MHz, CD$_3$OD) δ 7.61 (s, 1H), 7.45 (m, 2H), 6.90 (t, J=1.1 Hz, 1H), 6.55 (d, J=9.6 Hz, 1H), 3.31 (t, J=7.1 Hz, 2H), 2.20 (s, 3H), 1.66 (sext, J=7.2 Hz, 2H), 0.95 (t, J=7.4 Hz, 3H); $^{13}$C NMR (125 MHz, CD$_3$OD) δ 155.5, 138.5, 137.6, 130.9, 127.7, 126.8, 125.7, 125.4, 121.4, 113.6, 44.8, 22.9, 15.6, 12.0; HPLC $t_R$=13.5 min (Luna), 98.7%; ES-MS: (M+H)=273 m/z.

Example 5

(E)-4-(3-(Hex-1-enyl)imidazo[1,2-b]pyridazin-6-yl) morpholine fumarate

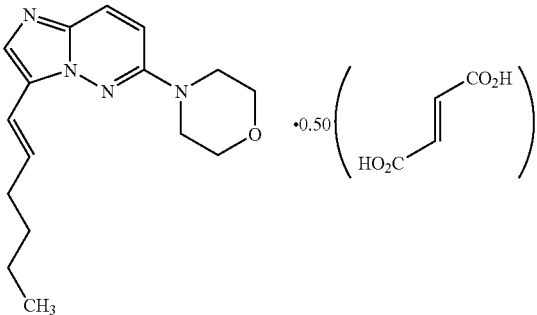

Prepared from the product of step A (example 3) and (E)-1-hexeneboronic acid according to general procedure 2. Treatment with fumaric acid (0.5 equiv) in methanol (1 mL) provided the fumarate salt of the title compound (81 mg, 100%) as a white solid: $^1$H NMR (500 MHz, DMSO-$d_6$) δ 7.85 (d, J=9.9 Hz, 1H), 7.63 (s, 1H), 7.13 (d, J=9.9 Hz, 1H), 6.70-6.60 (m+s, 3H), 3.75 (t, J=4.8 Hz, 4H), 3.47 (t, J=5.0 Hz, 4H), 2.24 (quart, J=7.0 Hz, 2H), 1.46-1.43 (m, 2H), 1.42-1.34 (m, 2H), 0.91 (t, J=7.3 Hz, 3H); $^{13}$C NMR (75 MHz, DMSO-$d_6$) δ 165.9, 154.8, 136.3, 133.9, 130.8, 130.2, 126.1, 125.7, 115.6, 109.0, 65.6, 45.8, 32.6, 31.0, 21.5, 13.7; HPLC $t_R$=13.0 min (Luna), >99%; ES-MS: (M+H)=287 m/z.

Example 6

(E)-3-(3-(Hex-1-enyl)imidazo[1,2-b]pyridazin-6-ylamino)propan-1-ol fumarate

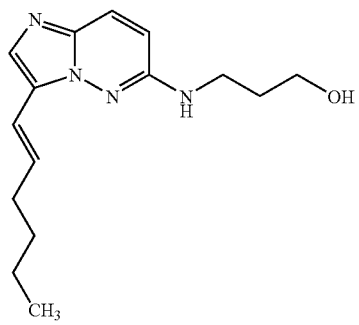

Step A: 3-(3-Bromoimidazo[1,2-b]pyridazin-6-ylamino)propan-1-ol

Prepared from 3-bromo-6-chloroimidazo[1,2-b]pyridazine and 3-amino-1-propanol according to general procedure 1 providing the amino compound (493 mg, 84%) as a yellow solid: $R_f$=0.56 (CH$_2$Cl$_2$/MeOH/NH$_4$OH, 160:18:2); $^1$H NMR (500 MHz, CD$_3$OD) δ 7.56 (d, J=9.7 Hz, 1H), 7.41 (s, 1H), 6.71 (d, J=9.7 Hz, 1H), 3.71 (t, J=6.3 Hz, 2H), 3.50 (t, J=6.8 Hz, 2H), 1.93 (quin, J=6.6 Hz, 2H); ES-MS: (M+H)=271, 273 m/z.

Step B: Prepared from the product of step A and (E)-1-hexeneboronic acid according to general procedure 2 providing the title compound (45 mg, 83%) as a grey solid; $^1$H NMR (500 MHz, CD$_3$OD) δ 7.56 (d, J=7.7 Hz, 1H), 7.48 (s, 1H), 6.78 (dt, J=7.1, 16.1 Hz, 1H), 6.72 (s, 1H), 6.70 (t, J=7.7 Hz, 1H), 6.60 (d, J=16.2 Hz, 1H), 3.70 (t, J=6.3 Hz, 2H), 3.46 (t, J=6.9 Hz, 2H), 2.31-2.26 (m, 2H), 1.94-1.89 (m, 2H), 1.53-1.47 (m, 2H), 1.44-1.40 (m, 2H), 0.79-0.94 (t, J=7.2 Hz, 3H); $^{13}$C NMR (125 MHz, CD$_3$OD) δ 169.3, 155.6, 137.0, 135.6, 134.0, 128.9, 127.0, 124.7, 116.5, 114.7, 60.8, 39.6, 34.4, 32.8, 32.6, 23.4, 14.3; HPLC $t_R$=11.6 min (Luna), 95.0%; ES-MS: (M+H)=275 m/z.

Example 7

(E)-3-(Hex-1-enyl)-N-(2-methoxyethyl)imidazo[1,2-b]pyridazin-6-amine fumarate

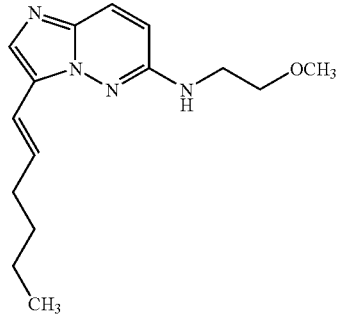

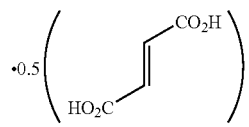

Step A: 3-bromo-N-(2-methoxyethyl)imidazo[1,2-b]pyridazin-6-amine

Prepared from 3-bromo-6-chloroimidazo[1,2-b]pyridazine and 2-methoxyethylamine according to general procedure 1 providing the amino compound (432 mg, 74%) as a yellow solid: $R_f$=0.71 (CH$_2$Cl$_2$/MeOH/NH$_4$OH, 160:18:2); $^1$H NMR (500 MHz, CD$_3$OD) δ 7.57 (d, J=9.7 Hz, 1H), 7.42 (s, 1H), 6.75 (d, J=9.7 Hz, 1H), 3.68 (t, J=5.4 Hz, 2H), 3.59 (t, J=5.6 Hz, 2H), 3.43 (s, 3H); ES-MS: (M+H)=271, 273 m/z.

Step B: Prepared from the product of step A and (E)-1-hexeneboronic acid according to general procedure 2 providing the title compound (78 mg, 47%) as a yellow solid; $^1$H NMR (500 MHz, CD$_3$OD) δ 7.58 (d, J=9.7 Hz, 1H), 7.45 (s, 1H), 6.77-6.70 (singlet overlapping with multiplet, 3H), 6.61 (d, J=16.1 Hz, 1H), 3.65 (t, J=5.5 Hz, 2H), 3.55 (t, J=5.5 Hz, 2H), 3.40 (s, 3H), 2.28 (q, J=6.9 Hz, 2H), 1.51-1.47 (m, 2H), 1.44-1.39 (m, 2H), 0.95 (t, J=7.2 Hz, 3H); $^{13}$C NMR (75

MHz, CD₃OD) δ 169.4, 155.5, 137.3, 135.6, 133.8, 128.8, 127.5, 125.0, 116.5, 114.4, 71.6, 59.0, 42.3, 34.4, 32.8, 23.8, 14.3; HPLC $t_R$=13.1 min (Luna), 98.6%; ES-MS: (M+H)= 275 m/z.

Example 8

(E)-N$^1$-(3-(Hex-1-enyl)imidazo[1,2-b]pyridazin-6-yl)-N$^2$,N$^2$-dimethylethane-1,2-diamine fumarate

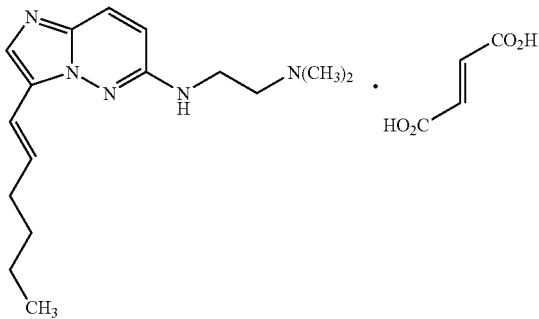

Step A: N$^1$-(3-Bromoimidazo[1,2-b]pyridazin-6-yl)-N$^2$,N$^2$-dimethylethane-1,2-diamine Prepared from 3-bromo-6-chloroimidazo[1,2-b]pyridazine and 2-(dimethylamino)ethylamine according to general procedure 1 providing the amino compound (456 mg, 74%) as a white solid; R$_f$=0.43 (CH₂Cl₂/MeOH/NH₄OH, 160:18:2); ¹H NMR (500 MHz, CD₃OD) δ 7.65 (d, J=9.6 Hz, 1H), 7.46 (s, 1H), 6.77 (d, J=9.7 Hz, 1H), 3.83 (t, J=5.9 Hz, 2H), 3.48 (t, J=6.0 Hz, 2H), 3.01 (s, 6H); ES-MS: (M+H)= 284, 286 m/z.

Step B: Prepared from the product of step A and (E)-1-hexeneboronic acid according to general procedure 2. Treatment with fumaric acid (0.99 equiv) in methanol (1 mL) provided the fumarate salt of the title compound (54 mg, 27%) as a light brown solid; ¹H NMR (500 MHz, CD₃OD) δ 7.60 (d, J=7.6 Hz, 1H), 7.50 (s,1H), 6.68-6.61 (m, 5H), 3.80 (t, J=5.9 Hz, 2H), 3.45 (t, J=5.9 Hz, 2H), 2.53 (s, 6H), 2.30-2.26 (m, 2H), 1.51-1.47 (m, 2H), 1.43-1.38 (m, 2H), 0.97 (t, J=7.1 Hz, 3H); ¹³C NMR (125 MHz, CD₃OD) δ 171.4, 155.15, 137.9, 136.3, 133.4, 128.9, 128.8, 126.1, 116.6, 113.5, 57.1, 43.9, 38.0, 34.3, 32.8, 23.4, 14.3 (one signal overlapping with solvent); HPLC $t_R$=9.1 min (Luna), 95.4%; ES-MS: (M+H)=288 m/z.

Example 9

(E)-3-(Hex-1-enyl)-N-(pyridin-2-ylmethyl)imidazo[1,2-b]pyridazin-6-amine fumarate

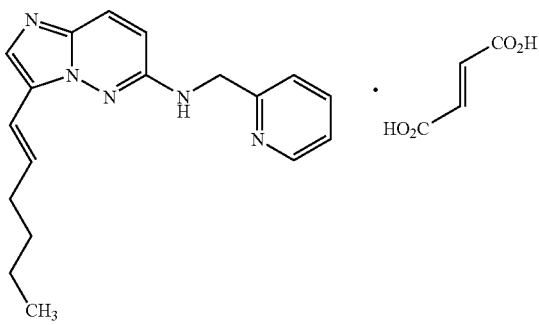

Prepared from the product of step A (example 1) and (E)-1-hexeneboronic acid according to general procedure 2. Treatment with fumaric acid (0.99 equiv) in methanol (1 mL) provided the fumarate salt of the title compound (30 mg, 21%) as a yellow solid; ¹H NMR (500 MHz, CD₃OD) δ 8.51 (d, J=4.8 Hz, 1H), 7.78 (dt, J=1.9, 9.4 Hz, 1H), 7.65 (d, J=9.7 Hz, 1H), 7.50 (d, J=7.9 Hz, 1H), 7.45 (s, 1H), 7.30 (dd, J=7.0, 5.2 Hz, 1H), 6.85 (d, J=9.7 Hz, 1H), 6.73 (s, 2H), 6.54 (dt, J=16.1, 7.0 Hz, 1H), 6.42 (d, J=16.1 Hz, 1H), 4.68 (s, 2H), 2.16 (q, J=6.7 Hz, 2H), 1.40-1.31 (m, 4H), 0.92 (t, J=7.1 Hz, 3H); ¹³C NMR (125 MHz, CD₃OD) δ 168.7, 160.0, 155.2, 153.9, 149.6, 138.8, 137.2, 135.4, 134.0, 128.8, 127.4, 125.1, 123.6, 122.8, 116.2, 114.3, 34.3, 32.6, 23.3, 14.3; HPLC $t_R$=9.5 min (Luna), 96.6%; ES-MS: (M+H)=308 m/z.

Example 10

(E)-2-(3-(Hex-1-enyl)imidazo[1,2-b]pyridazin-6-ylamino)butan-1-ol

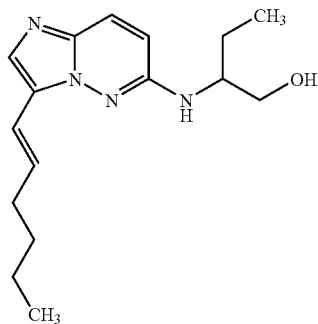

Step A: 2-(3-Bromoimidazo[1,2-b]pyridazin-6-ylamino)butan-1-ol

Prepared from 3-bromo-6-chloroimidazo[1,2-b]pyridazine and 2-aminobutan-1-ol according to general procedure 1 providing the amino compound (70 mg, 18%) as yellow solid; R$_f$=0.53 (CH₂Cl₂/MeOH/NH₄OH, 160:18:2); ¹H NMR (500 MHz, CDCl₃) δ 7.59 (d, J=9.5 Hz, 1H), 7.48 (s, 1H), 6.45 (d, J=9.5 Hz, 1H), 4.51 (d, J=6.3 Hz, 1H), 3.97-3.90 (m, 2H), 3.75-3.72 (m, 1H), 2.65 (br, 1H), 1.76-1.64 (m, 2H), 1.04 (t, 3H); ES-MS: (M+H)=285, 287 m/z.

Step B: Prepared from the product of step A and (E)-1-hexeneboronic acid according to general procedure 2 providing the title compound (27 mg, 38%) as an off-white solid; ¹H NMR (500 MHz, CD₃OD) δ 7.51 (d, J=9.7 Hz, 1H), 7.40 (s, 1H), 6.76-6.70 (m, 1H), 6.66 (d, J=9.7 Hz, 1H), 6.61 (d, J=16.1 Hz, 1H), 3.93-3.89 (m, 1H), 3.70-3.67 (m, 2H), 2.35-2.30 (m, 2H), 1.81-1.76 (m, 1H), 1.69-1.65 (m, 1H), 1.53-1.48 (m, 2H), 1.45-1.40 (m, 2H), 1.04-1.01 (t, J=7.3 Hz, 3H), 0.55 (t, J=7.3 Hz, 3H); ¹³C NMR (75 MHz, CD₃OD) δ 155.6, 138.2, 133.3, 129.1, 128.9, 125.8, 117.2, 114.1, 64.2, 56.1, 34.8, 33.2, 35.4, 23.7, 14.7, 11.4; HPLC $t_R$=12.9 min (Luna), 95.1%; ES-MS: (M+H)=289 m/z.

Example 11

N¹,N¹-Dimethyl-N²-(3-methylimidazo[1,2-b]pyridazin-6-yl)ethane-1,2-diamine

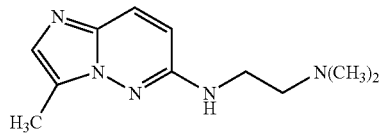

Prepared from the product of step A (example 8) according to general procedure 5 providing the title compound (90 mg, 68%) as a white solid; $^1$H NMR (500 MHz, CDCl$_3$) δ 7.55 (d, J=9.5 Hz, 1H), 7.27 (s, 1H), 6.38 (d, J=9.5 Hz, 1H), 4.95 (br, 1H), 3.45-3.43 (m, 2H), 2.57 (t, J=6.0 Hz, 2H), 2.43 (s, 3H), 2.27 (s, 6H); $^{13}$C NMR (125 MHz, CDCl$_3$) δ 153.1, 136.3, 129.2, 125.6, 124.7, 110.2, 57.6, 45.2, 38.9, 8.6; HPLC $t_R$=7.9 min (Synergi), 98.1%; ES-MS: (M+H)=220 m/z.

Example 12

N-(2-Methoxyethyl)-3-methylimidazo[1,2-b]pyridazin-6-amine

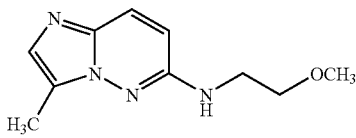

Prepared from the product of step A (example 7) according to general procedure 5 providing the title compound (46 mg, 62%) as a white solid; $^1$H NMR (500 MHz, CDCl$_3$) δ 7.57 (d, J=9.6 Hz, 1H), 7.28 (s, 1H), 6.35 (d, J=9.6 Hz, 1H), 4.65 (br, 1H), 3.65-3.63 (m, 2H), 3.60-3.57 (m, 2H), 3.41 (s, 3H), 2.43 (s, 3H); $^{13}$C NMR (125 MHz, CDCl$_3$) δ 152.9, 136.3, 129.4, 125.8, 124.8, 110.0, 70.6, 58.8, 41.4, 8.6; HPLC $t_R$=8.9 min (Synergi), 98.6%; ES-MS: (M+H)=207 m/z.

Example 13

3-Chloro-N-(pyridin-2-ylmethyl)imidazo[1,2-b]pyridazin-6-amine

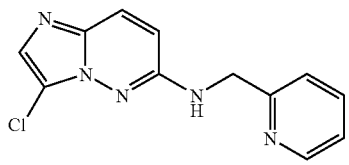

Prepared from 3,6-dichloroimidazo[1,2-b]pyridazine and 2-(aminomethyl)pyridine according to general procedure 3 providing the title compound (56 mg, 27%) as a white solid; $^1$H NMR (500 MHz, CD$_3$OD) δ 8.50 (d, J=4.9 Hz, 1H), 7.79 (dt, J=1.7, 9.4, Hz, 1H), 7.61 (d, J=9.7 Hz, 1H), 7.54 (d, J=7.9 Hz, 1H), 7.34 (s, 1H), 7.30 (dd, J=5.3, 6.5 Hz, 1H), 6.81 (d, J=9.7 Hz, 1H), 4.68 (s, 1H); $^{13}$C NMR (75 MHz, CD$_3$OD) δ 159.7, 155.5, 149.7, 138.7, 127.9, 126.1, 123.7, 123.6, 115.7, 114.6 (one carbon overlapping with solvent); HPLC $t_R$=8.8 min (Synergi), 98.8 %; ES-MS: (M+H)=260 m/z.

Example 14

3-Chloro-N-(3-morpholinopropyl)imidazo[1,2-b]pyridazin-6-amine hydrochloride

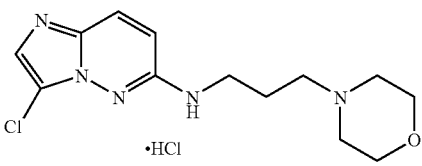

Prepared from 3,6-dichloroimidazo[1,2-b]pyridazine and 3-morpholinopropylamine according to general procedure 3. The free base was converted to the HCl salt with 2N HCl in Et$_2$O to provide the title compound (153 mg, 57%) as a white solid; $^1$H NMR (500 MHz, CD$_3$OD) δ 7.60 (d, J=9.7 Hz, 1H), 7.39 (s, 1H), 6.70 (d, J=9.7 Hz, 1H), 3.90 (br, 4H), 3.53 (t, J=6.7 Hz, 2H), 3.35-3.27 (m, 6H), 2.20-2.14 (m, 2H): $^{13}$C NMR (75 MHz, CD$_3$OD) δ 155.8, 137.2, 127.9, 126.1, 115.6, 114.7, 65.2, 56.8, 53.4, 39.6, 24.5; HPLC $t_R$=8.9 min (Synergi), >99%; ES-MS: (M+H)=332 m/z.

Example 15

3-Methyl-N-(pyridin-2-ylmethyl)imidazo[1,2-b]pyridazin-6-amine hydrochloride

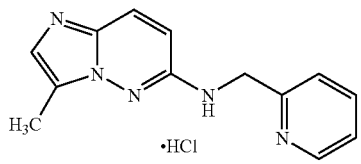

Prepared from the product of step A (example 1) according to general procedure 5. The free base was converted to the HCl salt with 2N HCl in Et$_2$O to provide the title compound (31 mg, 56%) as a white solid; $^1$H NMR (500 MHz, CD$_3$OD) δ 8.66 (d, J=5.0 Hz, 1H), 8.04 (t, J=7.3 Hz, 1H), 7.96 (d, J=9.8 Hz, 1H), 7.72 (d, J=7.9 Hz, 1H), 7.64 (s, 1H), 7.52 (t, J=6.2 Hz, 1H), 7.33 (d, J=9.8 Hz, 1H), 4.80 (s, 2H), 2.36 (s, 3H); $^{13}$C NMR (75 MHz, CD$_3$OD) δ 158.11, 156.5, 147.8, 141.5, 133.4, 128.6, 124.9, 124.6, 121.6, 120.2, 118.9, 46.7, 8.2; HPLC $t_R$=5.4 min (Synergi), 98.3%; ES-MS: (M+H)=240 m/z.

Example 16

3-Methyl-N-(3-morpholinopropyl)imidazo[1,2-b]pyridazin-6-amine fumarate

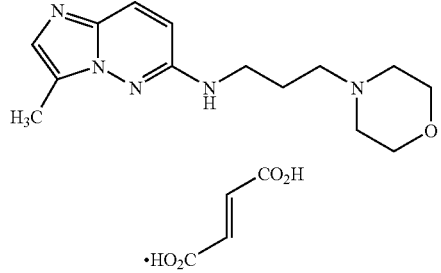

Step A: 3-Bromo-N-(3-morpholinopropyl)imidazo[1,2-b]pyridazin-6-amine

Prepared from 3-bromo-6-chloroimidazo[1,2-b]pyridazine and 3-morpholinopropylamine according to general procedure 1 providing the amino compound (1.30 g, 59%) as an orange oil; $R_f$=0.66 (CH$_2$Cl$_2$/MeOH/NH$_4$OH, 160:18:2); $^1$H NMR (500 MHz, CD$_3$OD) δ 7.54 (d, J=9.7 Hz, 1H), 7.39 (s, 1H), 6.47 (d, J=9.7 Hz, 1H), 3.71-3.69 (m, 4H), 3.42 (t, J=6.9 Hz, 2H), 2.51-2.48 (m, 6H), 1.92-1.89 (m, 2H); ES-MS: (M+H)=340, 342 m/z.

Step B: Prepared from the product of step A according to general procedure 5. Treatment with fumaric acid (1 equiv) in methanol (1 mL) provided the fumarate salt of the title compound (65 mg, 58%) as a white solid; $^1$H NMR (500 MHz, CD$_3$OD) δ 7.59 (d, J=9.7 Hz, 1H), 7.27 (s, 1H), 6.70 (d, J=9.7 Hz, 1H), 6.66 (s, 2H), 3.83-3.81 (m, 4H), 3.46 (t, J=6.5 Hz, 2H), 2.98-2.94 (m, 6H), 2.43 (s, 3H), 2.06 (m, 2H); $^{13}$C NMR (75 MHz, CD$_3$OD) δ 170.9, 155.6, 136.3, 136.0, 126.6, 126.5, 124.6, 114.6, 66.1, 57.1, 53.8, 40.0, 25.0, 8.6; HPLC $t_R$=6.1 min (Synergi), 95.4%; ES-MS: (M+H)=276 m/z.

Example 17

3-Hexyl-N-(3-morpholinopropyl)imidazo[1,2-b]pyridazin-6-amine hydrochloride

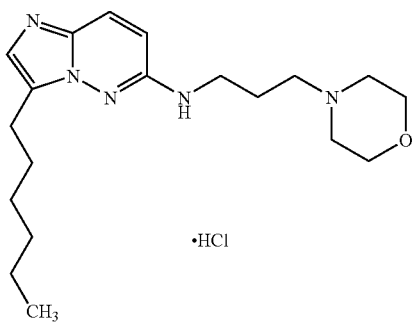

Step A: (E)-3-(Hex-1-enyl)-N-(3-morpholinopropyl)imidazo[1,2-b]pyridazin-6-amine Prepared from the product of step A (example 16) and (E)-1-hexeneboronic acid according to general procedure 2 providing the alkene (100 mg, 90%) as a brown oil; $^1$H NMR (500 MHz, CD$_3$OD) δ 7.51 (d, J=9.6 Hz, 1H), 7.41 (s, 1H), 6.75 (dt, J=7.0, 16.1 Hz, 1H), 6.62-6.58 (m, 2H), 3.70 (t, J=4.8 Hz, 4H), 3.41 (t, J=6.9 Hz, 2H), 2.52 (m, 6H), 2.30-2.26 (m, 2H), 1.94-1.88 (m, 2H), 1.52-1.41 (m, 4H), 0.96 (t, J=7.3 Hz, 3H).

Step B: The product from step A was dissolved in ethanol (5 mL) with 5% palladium on charcoal and placed under hydrogen (50 psi) in a Parr shaker. After 24 hr, the reaction mixture was filtered through celite and concentrated. The free-base was converted to the HCl salt with 2N HCl in Et$_2$O to provide the title compound (35 mg, 32%) as a white solid; $^1$H NMR (500 MHz, CD$_3$OD) δ 7.78 (d, J=9.8 Hz, 1H), 7.52 (s, 1H), 7.30 (d, J=9.8 Hz, 1H), 3.91 (m, 4H), 3.54 (t, J=6.6 Hz, 2H), 3.25-3.20 (m, 6H), 2.95-2.93 (m, 2H), 2.19-2.15 (m, 2H), 1.81-1.76 (m, 2H), 1.44-1.35 (m, 6H), 0.91 (t, J=7.0 Hz, 3H); $^{13}$C NMR (75 MHz, CD$_3$OD) δ 156.1, 134.6, 132.0, 122.7, 121.7, 118.2, 65.4, 56.8, 53.5, 32.7, 30.1, 27.9, 24.2, 24.0, 23.7, 14.4 (one peak overlapping with solvent); HPLC $t_R$=10.4 min (Synergi), 98.7%; ES-MS: (M+H)=346 m/z.

Example 18

(E)-N-(3-Morpholinopropyl)-3-(pent-1-enyl)imidazo[1,2-b]pyridazin-6-amine hydrochloride

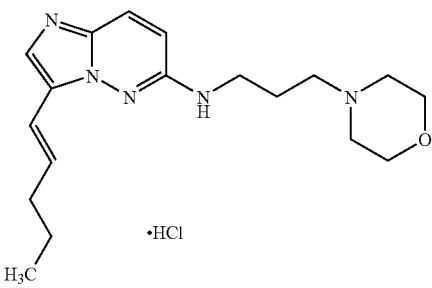

Prepared from the product of step A (example 16) and (E)-1-penteneboronic acid according to general procedure 2. The free base was converted to the HCl salt with 2N HCl in Et$_2$O to provide the title compound (58 mg, 55%) as a brown solid; $^1$H NMR (500 MHz, CD$_3$OD) δ 7.65 (d, J=9.7 Hz, 1H), 7.56 (s, 1H), 6.77-6.63 (m, 3H), 3.91-3.89 (m, 4H), 3.54 (t, J=6.4 Hz, 2H), 3.24-3.21 (m, 6H), 2.27 (q, J=6.8 Hz, 2H), 2.20-2.14 (m, 2H), 1.58-1.51 (m, 2H), 0.98 (t, J=7.4 Hz, 3H); $^{13}$C NMR (125 MHz, CD$_3$OD) δ 155.6, 136.8, 134.2, 129.2, 126.4, 124.8, 116.4, 115.0, 65.4, 57.0, 53.5, 39.8, 36.8, 24.4, 23.7, 14.1; HPLC $t_R$=9.3 min (Synergi), 97.3%; ES-MS: (M+H)=330 m/z.

Example 19

(E)-3-(Pent-1-enyl)-N-(pyridin-2-ylmethyl)imidazo[1,2-b]pyridazin-6-amine hydrochloride

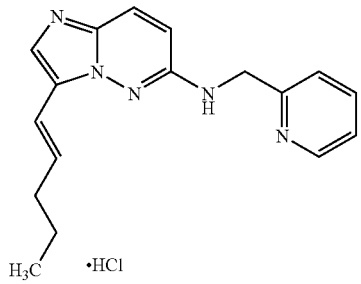

Prepared from the product of step A (example 1) and (E)-1-penteneboronic acid according to general procedure 2. The free-base was converted to the HCl salt with 2N HCl in Et$_2$O to provide the title compound (39 mg, 36%) as a brown solid; $^1$H NMR (500 MHz, CD$_3$OD) δ 8.61-8.60 (m, 1H), 8.07-8.04 (m, 1H), 7.97 (d, J=9.9 Hz, 1H), 7.89 (s, 1H), 7.73 (d, J=8.0 Hz, 1H), 7.54 (t, J=6.1 Hz, 1H), 7.34 (d, J=9.8 Hz, 1H), 6.66 (dt, J=7.0, 16.2 Hz, 1H), 6.47 (d, J=16.2 Hz, 1H), 4.83 (s, 2H), 2.23-2.19 (m, 2H), 1.50-1.45 (m, 2H), 0.95 (t, J=7.5 Hz, 3H); $^{13}$C NMR (75 MHz, CD$_3$OD) δ 158.1, 156.9, 147.8, 141.8, 138.9, 133.7, 130.1, 125.0, 124.4, 121.9, 120.2, 118.5, 114.3, 46.9, 36.6, 23.2, 14.0; HPLC $t_R$=9.5 min (Synergi), 94.8%; ES-MS: (M+H)=294 m/z.

Example 20

3-Cyclohexenyl-N-(3-morpholinopropyl)imidazo[1,2-b]pyridazin-6-amine hydrochloride

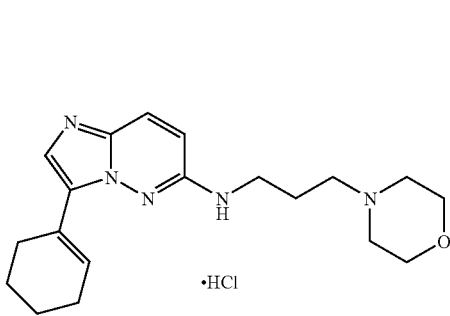

Prepared from the product of step A (example 16) and 1-cyclopenteneboronic acid according to general procedure 2. The free base was converted to the HCl salt with 2N HCl in Et$_2$O to provide the title compound (82 mg, 75%) as a brown solid; $^1$H NMR (500 MHz, CD$_3$OD) δ 7.66 (d, J=9.7 Hz, 1H), 7.47 (s, 1H), 7.13-7.12 (m, 1H), 6.78 (d, J=9.7 Hz, 1H), 3.89-3.87 (m, 4H), 3.49 (t, J=6.4 Hz, 2H), 3.21-3.17 (m, 6H), 2.51-2.49 (m, 2H), 2.32-2.30 (m, 2H), 2.17-2.12 (m, 2H), (1.84-1.81 (m, 2H), 1.75-1.70 (m, 2H); $^{13}$C NMR (75 MHz, CD$_3$OD) δ 155.4, 137.2, 131.1, 128.3, 126.6, 126.2, 124.8, 115.0, 65.4, 57.0, 53.6, 39.9, 27.9, 26.7, 24.3, 23.8, 23.2; HPLC t$_R$=9.1 min (Synergi), 98%; ES-MS: (M+H)=342 m/z.

Example 21

3-Cyclohexenyl-N-(pyridin-2-ylmethyl)imidazo[1,2-b]pyridazin-6-amine hydrochloride

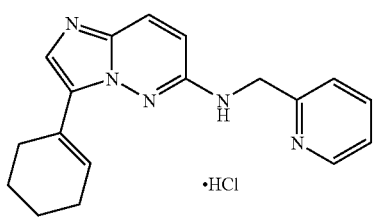

Prepared from the product of step A (example 1) and cyclopenteneboronic acid according to general procedure 2. The free-base converted to the HCl salt with 2N HCl in Et$_2$O to provide the title compound (70 mg, 64%) as a brown solid; $^1$H NMR (500 MHz, CD$_3$OD) δ 8.61 (d, J=5.2 Hz, 1H), 8.06 (d, J=7.7 Hz, 1H), 7.99 (d, J=9.9 Hz, 1H), 7.76 (s, 1H), 7.70 (d, J=7.9 Hz, 1H), 7.55-7.53 (m, 1H), 7.37 (d, J=9.9 Hz, 1H), 6.66-6.65 (m, 1H), 4.80 (s, 2H), 2.26-2.24 (m, 2H), 2.16-2.14 (m, 2H), 1.74-1.62 (m, 4H); $^{13}$C NMR (75 MHz, CD$_3$OD) δ 157.0, 156.5, 147.6, 141.9, 134.0, 132.5, 124.9, 124.7, 124.0, 121.9, 120.1, 118.5, 46.9, 27.5, 26.6, 23.5, 22.8; HPLC t$_R$=9.0 min (Synergi), 98.6%; ES-MS: (M+H)=306 m/z.

Example 22

(E)-3-(Hept-1-enyl)-N-(3-morpholinopropyl)imidazo[1,2-b]pyridazin-6-amine hydrochloride

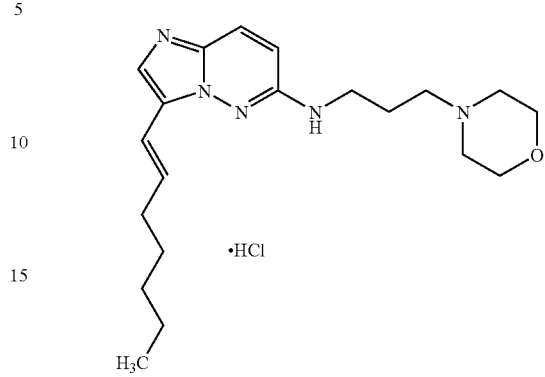

Prepared from the product of step A (example 16) and 1-(E)-1-hepteneboronic acid according to general procedure 2. The free base was converted to the HCl salt with 2N HCl in Et$_2$O to provide the title compound (65 mg, 57%) as a brown solid; $^1$H NMR (500 MHz, CD$_3$OD) δ 7.68 (d, J=9.7 Hz, 1H), 7.63 (s, 1H), 6.83 (d, J=9.7 Hz, 1H), 6.73-6.64 (m, 2H), 3.91-3.89 (m, 4H), 3.53 (t, J=6.5 Hz, 2H), 3.27-3.24 (m, 6H), 2.32-2.28 (m, 2H), 2.21-2.15 (m, 2H), 1.54-1.50 (m, 2H), 1.39-1.36 (m, 4H), 0.93 (t, J=7.0 Hz, 3H); $^{13}$C NMR (125 MHz, CD$_3$OD) δ155.9, 135.3, 125.1, 124.4, 115.9, 65.3, 56.9, 53.5 39.7, 34.7, 32.7, 30.3, 24.3, 23.7, 14.5 (quaternary Ar—C's did not show); HPLC t$_R$=11.1 min (Synergi), 95.4%; ES-MS: (M+H)=358 m/z.

Example 23

(E)-3-(hept-1-enyl)-N-(pyridin-2-ylmethyl)imidazo[1,2-b]pyridazin-6-amine hydrochloride

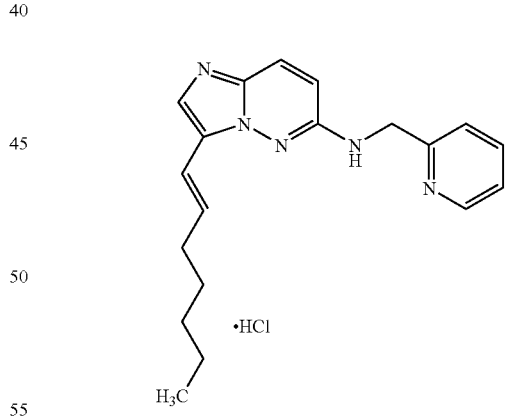

Prepared from the product of step A (example 1) and 1-(E)-1-hepteneboronic acid according to general procedure 2. The free base was converted to the HCl salt with 2N HCl in Et$_2$O to provide the title compound (38 mg, 34%) as a brown solid; $^1$H NMR (500 MHz, CD$_3$OD) δ 8.58-8.56 (m, 1H), 7.99-7.94 (m, 2H), 7.87 (s, 1H), 7.66 (d, J=7.9 Hz, 1H), 7.48-7.45 (m, 1H), 7.32 (d, J=9.9 Hz, 1H), 6.72-6.66 (dt, J=6.0, 16.2 Hz, 1H), 6.48 (d, J=9.9 Hz, 1H), 4.79 (s, 2H), 2.25-2.20 (m, 2H), 1.48-1.40 (m, 2H), 1.38-1.30 (m, 4H), 0.91 (t, J=6.9 Hz, 3H); $^{13}$C NMR (125 MHz, CD$_3$OD) δ 158.3, 156.7, 148.3, 140.8, 139.0, 133.6, 130.0, 124.6, 123.8, 121.7, 120.0, 118.5, 114.1, 47.2, 34.5, 32.5, 29.7, 23.6, 14.4; HPLC $t_R$=11.6 min (Synergi), 98.6%; ES-MS: (M+H)=322m/z.

Example 24

(6-(3-Morpholinopropylamino)imidazo[1,2-b]pyridazin-3-yl)methanol hydrochloride

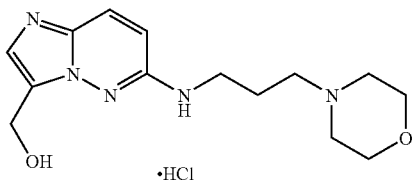

Prepared from (6-chloroimidazo[1,2-b]pyridazin-3-yl)methanol (7) and and 3-morpholinopropylamine according to general procedure 4 (StepB). The free base was converted to the HCl salt with 2N HCl in Et$_2$O to provide the title compound (174 mg, 65%) as a yellow solid; $^1$H NMR (500 MHz, CD$_3$OD) δ 7.58 (d, J=9.7 Hz, 1H), 7.63 (s, 1H), 6.98 (d, J=9.7 Hz, 1H), 4.89 (s, 2H), 3.93-3.91 (m, 4H), 3.55-3.52 (t, J=6.6 Hz, 2H), 3.34-3.25 (m, 6H), 2.22-2.16 (m, 2H); $^{13}$C NMR 75 MHz, CD$_3$OD) δ 156.3, 135.7, 130.7, 124.7, 123.5, 118.0, 65.1, 56.7, 53.5, 53.3, 39.6, 24.3; HPLC $t_R$=7.4 min (Synergi), 98.9%; ES-MS: (M+H)=292 m/z.

Example 25

(6-(Pyridin-2-ylmethylamino)imidazo[1,2-b]pyridazin-3-yl)methanol hydrochloride

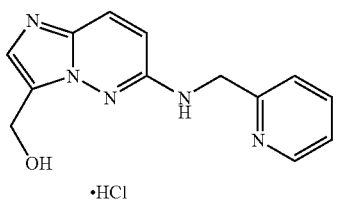

Prepared from (6-chloroimidazo[1,2-b]pyridazin-3-yl)methanol (7) and 2-(aminomethyl)pyridine according to general procedure 4 (StepB). The free base was converted to the HCl salt with 2N HCl in Et$_2$O to provide the title compound (48 mg, 20%) as a yellow solid; $^1$H NMR (300 MHz, CD$_3$OD) δ 8.49 (d, J=4.2 Hz, 1H), 7.77 (dt, J=1.7, 9.4 Hz, 1H), 7.61-7.52 (m, 2H), 7.35 (s, 1H), 7.31-7.26 (m, 1H), 6.77 (d, J=9.7 Hz, 1H), 4.74 (s, 2H), 4.67 (s, 2H); $^{13}$C NMR (75 MHz, CD$_3$OD) δ 160.2, 154.9, 149.6, 138.8, 137.8, 129.8, 129.5, 125.9, 123.7, 123.6, 114.2, 53.8, 47.6; HPLC $t_R$=7.0 min (Synergi), 96.1%; ES-MS: (M+H)=256 m/z.

Example 26

3-(Hex-1-ynyl)-N-(3-morpholinopropyl)imidazo[1,2-b]pyridazin-6-amine hydrochloride

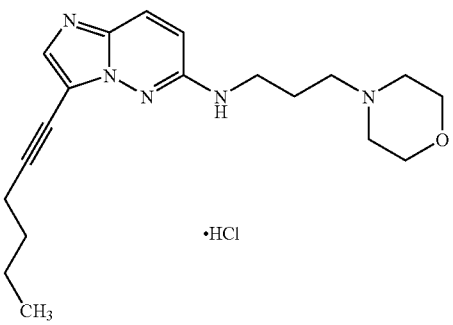

Prepared from the product of step A (example 16) according to general procedure 6. The free base was converted to the HCl salt with 2N HCl in Et$_2$O to provide the title compound (27 mg, 18%) as a brown solid; $^1$H NMR (500 MHz, CD$_3$OD) δ 7.67 (d, J=9.7 Hz, 1H), 7.60 (s, 1H), 6.83 (d, J=9.7 Hz, 1H), 3.95 (m, 4H), 3.54 (t, J=6.4 Hz, 2H), 3.34-3.24 (m, 6H), 2.56 (t, J=6.4 Hz, 2H), 2.21-2.15 (m, 2H), 1.67-1.54 (m, 4H), 0.99 (t, J=7.4 Hz, 3H); $^{13}$C NMR (125 MHz, CD$_3$OD) δ 156.1, 136.6, 132.2, 124.9, 116.5, 115.1, 100.7, 68.1, 65.1, 56.8, 53.4, 39.5, 31.8, 24.3, 23.0, 20.1, 14.0; HPLC $t_R$=12.7 min (Luna), 97.5%; ES-MS: (M+H)=342 m/z.

Example 27

(Z)-3-(Hex-1-enyl)-N-(3-morpholinopropyl)imidazo[1,2-b]pyridazin-6-amine hydrochloride

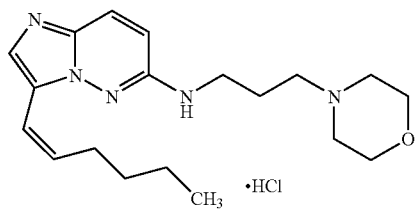

3-(Hex-1-ynyl)-N-(3-morpholinopropyl)imidazo[1,2-b]pyridazin-6-amine (75 mg, 0.22 mmol) was dissolved in ethanol (4 mL) and Lindlar's catalyst (20 mg) added. After degassing with a nitrogen stream for 10 mins, the reaction was put under a balloon of hydrogen for 48 h. The solids were filtered off and the filtrate was concentrated. The obtained residue was purified by semi-prep HPLC to provide the free-base, which was subsequently converted to the HCl salt with 2N HCl in Et$_2$O to provide the title compound (15 mg, 18%) as an orange solid; $^1$H NMR (300 MHz, CD$_3$OD) δ 7.67 (d, J=9.6 Hz, 1H), 7.61 (d, J=4.9 Hz, 1H), 6.81-6.74 (m, 2H), 5.88 (dt, J=7.2, 16.2 Hz, 1H), 3.89 (m, 4H), 3.52 (t, J=6.5 Hz, 2H), 3.37-3.22 (m, 6H), 2.44-2.37 (m, 2H), 2.21-2.12 (m, 2H), 1.56-1.39 (m, 4H), 0.95 (t, J=7.1 Hz, 3H); $^{13}$C NMR (75 MHz, CD$_3$OD) δ 155.6, 135.0, 127.9, 124.8, 115.8, 114.5, 65.3, 56.8, 53.4, 39.6, 32.6, 30.8, 24.5, 23.6, 14.3 (2 quaternary aromatic carbons did not show); HPLC $t_R$=13.1 min (Synergy), 91.7%; ES-MS: (M+H)=344 m/z.

Example 28

3-(Hex-1-ynyl)-N-(pyridin-2-ylmethyl)imidazo[1,2-b]pyridazin-6-amine hydrochloride

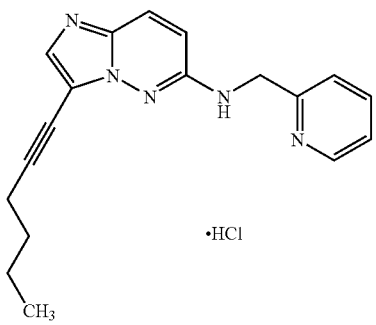

Prepared from the product of step A (example 1) according to general procedure 6. The free-base was converted to the HCl salt with 2N HCl in Et$_2$O to provide the title compound (56 mg, 16%) as a brown solid; $^1$H NMR (500 MHz, CD$_3$OD) δ 8.61-8.60 (m, 1H), 8.12-8.08 (dt, J=1.6, 7.8Hz, 1H), 7.88 (d, J=9.8 Hz, 1H), 7.80-7.78 (m, 2H), 7.58 (t, J=6.5 Hz, 1H), 7.21 (d, J=9.8 Hz, 1H), 4.81(s, 2H), 2.51 (t, J=6.9 Hz, 2H), 1.59-1.46 (m, 4H), 0.94 (t, J=7.3 Hz, 3H); $^{13}$C NMR (75 MHz, CD$_3$OD) δ 157.5, 156.1, 146.6, 141.6, 134.3, 127.0, 124.5, 122.7, 118.7, 115.3, 101.7, 65.9, 46.1, 31.0, 22.5, 19.5, 13.4 (one carbon overlapping with solvent); HPLC t$_R$=13.3 min (Synergi), 97.4%; ES-MS: (M+H)=306 m/z.

Example 29

3-Hexyl-N-(pyridin-2-ylmethyl)imidazo[1,2-b]pyridazin-6-amine hydrochloride 3-(Hex-1-ynyl)-N-(pyridin-2-ylmethyl)imidazo[1,2-b]pyridazin-6-amine was dissolved in ethanol (5 mL) with 5% palladium on charcoal and placed under hydrogen (50 psi) in a Parr shaker. After 24 hr, the reaction mixture was filtered through celite and concentrated to provide the free-base. This was converted to the HCl salt with 2N HCl in Et$_2$O to provide the title compound (26 mg, 41%) as an orange solid; $^1$H NMR (300 MHz, CD$_3$OD) δ 8.52 (d, J=5.0 Hz, 1H), 7.92 (d, J=9.8 Hz, 1H), 7.89-7.83 (dt, J=1.7, 9.4 Hz, 1H), 7.63 (s, 1H), 7.54 (d, J=7.9 Hz, 1H), 7.37-7.35 (m, 1H), 7.31 (d, J=9.8 Hz, 1H), 4.73 (s, 2H), 2.78 (t, J=7.4 Hz, 2H), 1.55-1.48 (m, 2H), 1.29-1.25 (m, 6H), 0.98 (t, J=6.6 Hz, 3H); $^{13}$C NMR (75 MHz, CD$_3$OD) δ 158.2, 156.2, 148.8, 139.0, 132.9, 131.9, 123.6, 122.8, 121.0, 119.8, 118.2, 46.9, 32.0, 29.3, 27.1, 23.2, 23.0, 13.8; HPLC t$_R$=9.26 min (Luna), 95.3%; ES-MS: (M+H)=310 m/z.

Example 30

3-(Methoxymethyl)-N-(3-morpholinopropyl)imidazo[1,2-b]pyridazin-6-amine hydrochloride Prepared from 6-chloro-3-(methoxymethyl)imidazo[1,2-b]pyridazine (8a) and 3-morpholinopropylamine according to general procedure 4 (step B). The free-base was converted to the HCl salt with 2N HCl in Et$_2$O to provide the title compound (35 mg, 31%) as a white solid; $^1$H NMR (500 MHz, CD$_3$OD) δ 7.67 (d, J=9.8 Hz, 1H), 7.54 (s, 1H), 6.80 (d, J=9.8 Hz, 1H), 4.76 (s, 2H), 3.90-3.89 (m, 4H), 3.51 (t, J=6.5 Hz, 2H), 3.38 (s, 3H), 3.26-3.23 (m, 6H), 2.18-2.13 (m, 2H); $^{13}$C NMR (125 MHz, CD$_3$OD) δ 154.7, 136.5, 128.7, 125.7, 124.2, 115.0, 64.3, 62.2, 57.3, 55.9, 52.5, 38.7, 23.6; HPLC t$_R$=8.1 min (Synergi), 95.2%; ES-MS: (M+H)=306 m/z.

Example 31

3-(Ethoxymethyl)-N-(3-morpholinopropyl)imidazo[1,2-b]pyridazin-6-amine hydrocloride Prepared from 6-chloro-3-(ethoxymethyl)imidazo[1,2-b]pyridazine (8b) and 3-morpholinopropylamine according to general procedure 4 (step B). The free-base was converted to the HCl salt with 2N HCl in Et$_2$O to provide the title compound (36 mg, 17%) as a white solid; $^1$H NMR (500 MHz, CD$_3$OD) δ 7.64 (d, J=9.7 Hz, 1H), 7.50 (s, 1H), 6.77 (d, J=9.7 Hz, 1H), 4.80 (s, 2H), 3.90-3.88 (m, 4H), 3.60 (q, J=7.1 Hz, 2H), 3.50 (t, J=6.4 Hz, 2H), 3.26-3.18 (m, 6H), 2.17-2.11 (m, 2H), 1.20 (t, J=7.0 Hz, 3H); $^{13}$C NMR (125 MHz, CD$_3$OD) δ 155.6, 137.5, 130.0, 127.0, 125.3, 115.5, 66.7, 65.5, 61.4, 57.0, 53.5, 39.7, 24.6,15.5; HPLC t$_R$=7.7 min (Luna), 97.6%; ES-MS: (M+H)=320 m/z.

Example 32

3-(Ethoxymethyl)-N-(pyridin-2-ylmethyl)imidazo[1,2-b]pyridazin-6-amine hydrochloride

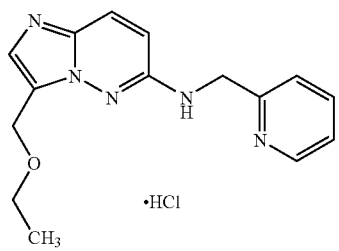

Prepared from 6-chloro-3-(ethoxymethyl)imidazo[1,2-b]pyridazine (8b) and 2-(aminomethyl)pyridine according to general procedure 4 (step B). The free-base was converted to the HCl salt with 2N HCl in Et$_2$O to provide the title compound (35 mg, 18%) as a white solid; $^1$H NMR (500 MHz, CD$_3$OD) δ 8.53-8.52 (m, 1H), 7.90 (d, J=9.7 Hz, 1H), 7.86 (dt, J=1.7, 9.5 Hz, 1H), 7.78 (s, 1H), 7.56 (d, J=9.8 Hz, 1H), 7.38-7.36 (m, 1H), 7.26 (d, J=9.8 Hz, 1H), 4.73 (s, 2H), 4.68 (s, 2H), 3.49 (q, J=7.0 Hz, 2H), 1.10 (t, J=7.1 Hz, 3H); $^{13}$C NMR (125 MHz, CD$_3$OD) δ 158.9, 156.6, 149.3, 139.6, 134.7, 128.7, 124.2, 123.6, 123.0, 122.5, 119.9, 67.5, 60.9, 47.4, 15.4; HPLC $t_R$=7.4 min (Luna), 98.5%; ES-MS: (M+H)= 284 m/z.

Example 33

N-(Pyridin-2-ylmethyl)imidazo[1,2-b]pyridazin-6-amine hydrochloride

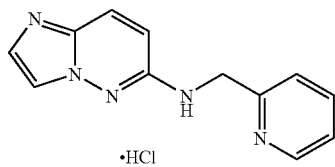

Prepared from 6-chloroimidazo[1,2-b]pyridazine (4) and 2-(aminomethyl)pyridine according to general procedure 2. The free-base was converted to the HCl salt with 2N HCl in Et$_2$O to provide the title compound (135 mg, 40%) as a white solid; $^1$H NMR (500 MHz, CD$_3$OD) δ 8.68-8.67 (m, 1H), 8.27 (dt, J=1.5, 9.4 Hz, 1H), 8.03 (d, J=10 Hz, 1H), 7.99-7.98 (m, 1H), 7.90-7.87 (m, 2H), 7.72 (t, J=6.5 Hz, 1H), 7.40 (d, J=10 Hz, 1H), 4.80 (s, J=Hz, 2H); $^{13}$C NMR (75 MHz, CD$_3$OD) δ 157.2, 156.8, 145.7, 144.4, 134.0, 125.9, 125.7, 122.3, 121.9, 121.4, 119.7, 45.5; HPLC $t_R$=6.3 min (Luna), 98.9%; ES-MS: (M+H)=226 m/z.

Example 34

3-(Ethoxymethyl)-N-(pyridin-2-ylmethyl)imidazo[1,2-b]pyridazin-6-amine hydrochloride

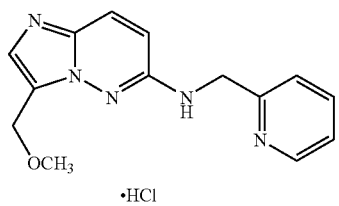

Prepared from 6-chloro-3-(methoxymethyl)imidazo[1,2-b]pyridazine (8a) and 2-(aminomethyl)pyridine according to general procedure 4 (step B). The free-base was converted to the HCl salt with 2N HCl in Et$_2$O to provide the title compound (13 mg, 12%) as a white solid; $^1$H NMR (500 MHz, CD$_3$OD) δ 8.56 (d, J=5.1 Hz, 1H), 7.95 (m, 2H), 7.84 (s, 1H), 7.63 (d, J=7.9 Hz, 1H), 7.43 (dd, J=5.8, 7.8 Hz, 1H), 7.31 (d, J=9.9 Hz, 1H), 4.75 (s, 2H), 4.64 (s, 2H), 3.30 (s, 3H); $^{13}$C NMR (75 MHz, CD$_3$OD) δ 158.4, 156.7, 148.7, 140.4, 134.5, 128.5, 124.5, 124.1, 122.4, 122.1, 120.5, 62.7, 58.8, 47.1; HPLC $t_R$=4.2 min (Luna), 95.7%; ES-MS: (M+H)=270 m/z.

Example 35

N-(3-Morpholinopropyl)imidazo[1,2-b]pyridazin-6-amine hydrochloride

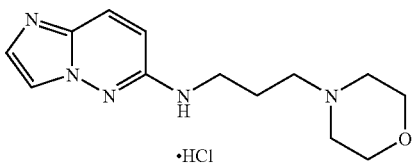

Prepared from 6-chloroimidazo[1,2-b]pyridazine (4) and 3-morpholinopropylamine according to general procedure 2. The free-base was converted to the HCl salt with 2N HCl in Et$_2$O to provide the title compound (125 mg, 32%) as a brown solid; $^1$H NMR (500 MHz, CD$_3$OD) δ 7.73 (s, 1H), 7.63 (d, J=9.8 Hz, 1H), 7.45 (d, J=1.2 Hz, 1H), 6.74 (d, J=9.8 Hz, 1H), 3.89-3.88 (m, 4H), 3.45 (t, J=6.6 Hz, 2H), 3.20-3.13 (m, 6H), 2.14-2.08 (m, 2H); $^{13}$C NMR (125 MHz, CD$_3$OD) δ 155.7, 137.0, 129.6, 125.2, 118.0, 115.8, 65.6, 56.9, 53.5, 39.7, 24.6; HPLC $t_R$=6.5 min (Luna), >99%; ES-MS: (M+H)=262 m/z.

Example 36

(E)-1-(3-(3-(Hex-1-enyl)imidazo[1,2-b]pyridazin-6-ylamino)propyl)pyrrolidin-2-one hydrochloride

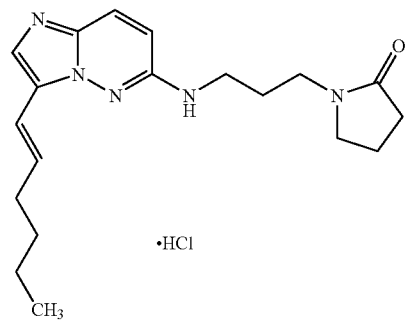

Step A: 1-(3-(3-Bromoimidazo[1,2-b]pyridazin-6-ylamino)propyl)pyrrolidin-2-one

Prepared from 3-bromo-6-chloroimidazo[1,2-b]pyridazine and 1-(3-aminopropyl)pyrrolidin-2-one according to general procedure 1 providing the intermediate (150 mg, 58%) as a white solid; R$_f$=0.58 (CH$_2$Cl$_2$/MeOH/NH$_4$OH, 160:18:2); $^1$H NMR (500 MHz, CD$_3$OD) δ 7.55 (d, J=9.7 Hz, 1H), 7.39 (s, 1H), 6.68 (d, J=9.7 Hz, 1H), 3.53 (t, J=7.1 Hz, 2H), 3.43-3.38 (m, 4H), 2.39 (t, J=8.0 Hz, 2H), 2.08 (quin, J=7.6 Hz, 2H), 1.94 (quin, J=6.9 Hz, 2H); ES-MS: (M+H)= 338, 340 m/z.

Step B: Prepared from the product of step A and (E)-1-hexeneboronic acid according to general procedure 2. The free-base was converted to the HCl salt with 2N HCl in Et$_2$O to provide the title compound (68 mg, 52%) as a brown solid; $^1$H NMR (500 MHz, CD$_3$OD) δ 7.90 (s, 1H), 7.86 (d, J=9.8 Hz, 1H), 7.16 (d, J=9.8 Hz, 1H), 6.89 (dt, J=6.1, 16.2 Hz, 1H), 6.68 (d, J=16.2 Hz, 1H), 3.50 (t, J=7.0 Hz, 2H), 3.44-3.40 (m, 4H), 2.38-2.32 (m, 4H), 2.09-2.03 (m, 2H), 1.98-1.93 (m, 2H), 1.56-1.50 (m, 2H), 1.46-1.40 (m, 2H), 0.98-0.96 (t, J=6.3 Hz, 3H); $^{13}$C NMR (125 MHz, CD$_3$OD) δ 177.8, 157.1, 139.0, 133.3, 130.1, 121.2, 120.6, 117.9, 114.3, 41.3, 39.9, 34.3, 32.4, 32.1, 26.9, 23.3, 18.9, 14.3 (one signal overlapping with solvent); HPLC t$_R$=11.4 min (Luna), 97.3%; ES-MS: (M+H)=342 m/z.

Example 37

(E)-4-(3-(Hex-1-enyl)imidazo[1,2-b]pyridazin-6-ylamino)butan-1-ol hydrochloride

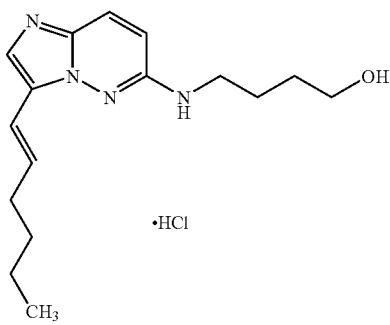

Step A: 4-(3-Bromoimidazo[1,2-b]pyridazin-6-ylamino)butan-1-ol

Prepared from 3-bromo-6-chloroimidazo[1,2-b]pyridazine and 4-aminobutan-1-ol according to general procedure 1 providing the intermediate (150 mg, 82%) as a yellow solid: R$_f$=0.45 (CH$_2$Cl$_2$/MeOH/NH$_4$OH, 160:18:2); $^1$H NMR (500 MHz, CD$_3$OD) δ 7.53 (d, J=9.7 Hz, 1H), 7.38 (s, 1H), 6.68 (d, J=9.7 Hz, 1H), 3.62 (t, J=6.6 Hz, 2H), 3.40 (t, J=6.9 Hz, 2H), 1.77-1.72 (m, 2H), 1.69-1.64 (m, 2H).

Step B: Prepared from the product of step A and (E)-1-hexeneboronic acid according to general procedure 2. The free base was converted to the HCl salt with 2N HCl in Et$_2$O to provide the title compound (61 mg, 51%) as a brown solid; $^1$H NMR (500 MHz, CD$_3$OD) δ 7.87 (s, 1H), 7.85 (d, J=9.8 Hz, 1H), 7.15 (,J=9.8 Hz, 1H), 6.93 (dt, J=7.0, 16.2 Hz, 1H), 6.66 (d, J=16.2 Hz, 1H), 3.62 (t, J=6.5 Hz, 2H), 3.43 (t, J=7.0 Hz, 2H), 2.37-2.32 (m, 2H), 1.82-1.76 (m, 2H), 1.69-1.64 (m, 2H), 1.56-1.50 (m, 2H), 1.47-1.41 (m, 2H), 0.96 (t, J=7.3 Hz, 3H); $^{13}$C NMR (125 MHz, CD$_3$OD) δ 157.1, 139.1, 133.3, 130.1, 120.9, 120.7, 117.7, 114.3, 62.6, 42.6, 34.2, 32.3, 31.2, 25.9, 23.3, 14.3; HPLC t$_R$=11.2 min (Luna), 98.3%; ES-MS: (M+H)=289 m/z.

Example 38

(E)-3-(Hex-1-enyl)-N-(3-(4-methylpiperazin-1-yl)propyl)imidazo[1,2-b]pyridazin-6-amine hydrochloride

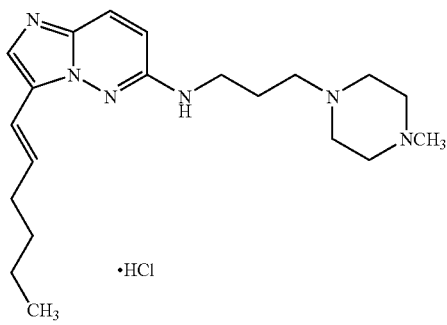

Step A: 3-Bromo-N-(3-(4-methylpiperazin-1-yl)propyl)imidazo[1,2-b]pyridazin-6-amine Prepared from 3-bromo-6-chloroimidazo[1,2-b]pyridazine and 3-(4-methylpiperazin-1-yl)propan-1-amine according to general procedure 1 providing the intermediate (200 mg, 85%) as a clear oil: R$_f$=0.25 (CH$_2$Cl$_2$/MeOH/NH$_4$OH, 160:18:2); $^1$H NMR (500 MHz, CD$_3$OD) δ 7.54 (d, J=9.6 Hz, 1H), 7.39 (s, 1H), 6.67 (d, J=9.7 Hz, 1H), 3.42 (t, J=7.0 Hz, 2H), 2.53-2.50 (m, 10H), 2.29 (s, 3H), 1.91 (quin, J=6.6 Hz, 2H)

Step B: Prepared from the product of step A and (E)-1-hexeneboronic acid according to general procedure 2. The free-base was converted to the HCl salt with 2N HCl in Et$_2$O to provide the title compound (60 mg, 35%) as a brown solid; $^1$H NMR (500 MHz, CD$_3$OD) δ 7.59 (d, J=9.7 Hz, 1H), 7.50 (s, 1H), 6.77-6.69 (m, 2H), 6.61 (d, J=16.2 Hz, 1H), 3.45 (t, J=6.7 Hz, 2H), 3.35 (m, 2H), 3.13-2.69 (m, 11H), 2.29 (q, J=6.7 Hz, 2H), 2.02-1.93 (m, 2H), 1.53-1.38 (m, 4H), 0.96 (t, J=7.1 Hz, $^{13}$C NMR (125 MHz, CD$_3$OD) δ 155.6, 137.1, 133.8, 128.9, 127.2, 125.0, 116.5, 114.6, 56.3, 54.5, 51.8, 44.1, 40.4, 34.4, 32.9, 26.2, 23.4, 14.4; HPLC t$_R$=8.7 min (Luna), 95.1%; ES-MS: (M+H)=357 m/z.

Example 39

(E)-N$^1$-(3-(Hex-1-enyl)imidazo[1,2-b]pyridazin-6-yl)-N$^3$,N$^3$-dimethylpropane-1,3-diamine hydrochloride

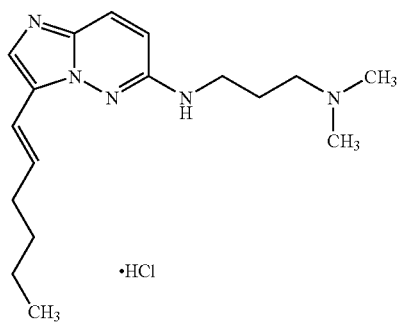

Step A: $N^1$-(3-Bromoimidazo[1,2-b]pyridazin-6-yl)-$N^3,N^3$-dimethylpropane-1,3-diamine Prepared from 3-bromo-6-chloroimidazo[1,2-b]pyridazine and $N^1,N^1$-dimethylpropane-1,3-diamine according to general procedure 1 providing the intermediate (160 mg, 84%) as a clear oil: $R_f$=0.16 ($CH_2Cl_2$/MeOH/$NH_4OH$, 160:18:2); $^1H$ NMR (500 MHz, $CD_3OD$) δ 7.54 (d, J=9.5 Hz, 1H), 7.39 (s, 1H), 6.68 (d, J=9.5 Hz, 1H), 3.40 (t, J=7.1 Hz, 2H), 2.48-2.45 (m, 2H), 2.27 (s, 6H), 1.93-1.88 (m, 2H); ES-MS: (M+H)=298, 300 m/z.

Step B: Prepared from the product of step A and (E)-1-hexeneboronic acid according to general procedure 2. The free-base was converted to the HCl salt with 2N HCl in $Et_2O$ to provide the title compound (31 mg, 40%) as a brown solid; $^1H$ NMR (500 MHz, $CD_3OD$) δ 7.63 (d, J=9.7 Hz, 1H), 7.55 (s, 1H), 6.74 (d, J=9.7 Hz, 1H), 6.69-6.66 (m, 2H), 3.52 (t, J=6.5 Hz, 2H), 3.29-3.26 (m, 2H), 2.90 (s, 6H), 2.32-2.38 (m, 2H), 2.18-2.16 (m, 2H), 1.54-1.48 (m, 2H), 1.46-1.39 (m, 2H), 0.96 (t, J=7.3 Hz, 3H); $^{13}C$ NMR (125 MHz, $CD_3OD$) δ 155.6, 137.0, 134.2, 129.1, 126.8, 125.0, 116.3, 114.7, 57.3, 43.6, 38.5, 34.4, 23.8, 25.1, 23.1, 14.3; HPLC $t_R$=9.2 min (Luna), 97.9%; ES-MS: (M+H)=302 m/z.

Example 40

(E)-$N^1,N^1$-Diethyl-$N^2$-(3-(hex-1-enyl)imidazo[1,2-b]pyridazin-6-yl)ethane-1,2-diamine hydrochloride

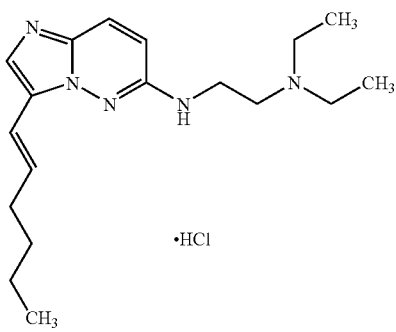

Step A: $N^1$-(3-Bromoimidazo[1,2-b]pyridazin-6-yl)-$N^2,N^2$-diethylethane-1,2-diamine Prepared from 3-bromo-6-chloroimidazo[1,2-b]pyridazine and $N^1,N^1$-diethylethane-1,2-diamine according to general procedure 1 providing the intermediate (160 mg, 80%) as a clear oil: $R_f$=0.22 ($CH_2Cl_2$/MeOH/$NH_4OH$, 160:18:2); $^1H$ NMR (500 MHz, $CD_3OD$) δ 7.55 (d, J=9.7 Hz, 1H), 7.40 (s, 1H), 6.68 (d, J=9.7 Hz, 1H), 3.52 (t, J=6.0 Hz, 2H), 2.79 (t, J=5.8 Hz, 2H), 2.68 (quart, J=7.2 Hz, 4H), 1.12 (t, J=7.2 Hz, 6H); ES-MS: (M+H)=312, 314 m/z.

Step B: Prepared from the product of step A and (E)-1-hexeneboronic acid according to general procedure 2. The free-base was converted to the HCl salt with 2N HCl in $Et_2O$ to provide the title compound (74 mg, 59%) as a brown solid; $^1H$ NMR (500 MHz, $CD_3OD$) δ 7.74 (d, J=9.6 Hz, 1H), 7.62 (s, 1H), 6.85 (d, J=9.6 Hz, 1H), 6.71-6.62 (m, 2H), 3.83 (t, J=6.3 Hz, 2H), 3.51 (t, J=6.4 Hz, 2H), 3.34 (q, J=7.0 Hz, 4H), 2.32-2.39 (m, 2H), 1.54-1.48 (m, 2H), 1.46-1.40 (m, 2H), 1.38-1.34 (t, J=7.3 Hz, 6H), 0.96 (t, J=7.3 Hz, 3H); $^{13}C$ NMR (125 MHz, $CD_3OD$) δ 155.7, 136.6, 135.3, 129.5, 125.7, 125.1, 115.8, 115.4, 51.0, 37.6, 34.4, 32.7, 23.4, 14.3, 9.2 (one signal overlapping with solvent); HPLC $t_R$=9.3 min (Luna), 96.7%; ES-MS: (M+H)=316 m/z.

Example 41

(E)-3-(Hex-1-enyl)-N-(3-methoxypropyl)imidazo[1,2-b]pyridazin-6-amine hydrochloride

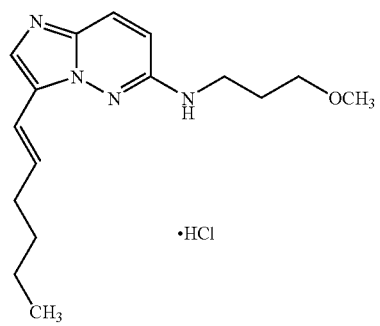

Step A: 3-Bromo-N-(3-methoxypropyl)imidazo[1,2-b]pyridazin-6-amine

Prepared from 3-bromo-6-chloroimidazo[1,2-b]pyridazine and 3-methoxypropylamine according to general procedure 1 providing the intermediate (43 mg, 54%) as a clear oil: $R_f$=0.55 ($CH_2Cl_2$/MeOH/$NH_4OH$, 160:18:2); $^1H$ NMR (500 MHz, $CD_3OD$) δ 7.53 (d, J=9.6 Hz, 1H), 7.39 (s, 1H), 6.68 (d, J=9.7 Hz, 1H), 3.53 (t, J=6.2 Hz, 2H), 3.44 (t, J=6.9 Hz, 2H), 3.36 (s, 3H), 1.95 (quin, J=6.5 Hz, 2H).

Step B: Prepared from the product of step A and (E)-1-hexeneboronic acid according to general procedure 2. The free base was converted to the HCl salt with 2N HCl in $Et_2O$ to provide the title compound (43 mg, 54%) as a brown solid; $^1H$ NMR (500 MHz, $CD_3OD$) δ 7.53 (d, J=9.7 Hz, 1H), 7.42 (s, 1H), 6.78 (dt, J=16.1, 7.0 Hz, 1H), 6.64-6.58 (m, 2H), 3.53 (t, J=6.2 Hz, 2H), 3.44 (t, J=6.2 Hz, 2H), 3.35 (s, 3H), 2.30-2.26 (m, 2H), 1.97-1.92 (m, 2H), 1.53-1.40 (m, 4H), 0.96 (t, J=7.3 Hz, 3H); $^{13}C$ NMR (125 MHz, $CD_3OD$) δ 157.1, 139.2, 133.2, 130.0, 121.0, 120.6, 117.8, 114.3, 71.4, 59.0, 40.0, 34.3, 32.3, 29.4, 23.3, 14.3; HPLC $t_R$=12.3 min, 98.6%; ES-MS: (M+H)=289 m/z.

Example 42

(E)-2-(3-(Hex-1-enyl)imidazo[1,2-b]pyridazin-6-ylamino)ethanol hydrochloride

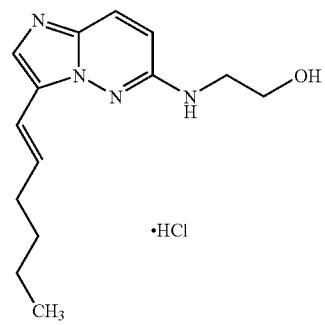

Step A: 2-(3-Bromoimidazo[1,2-b]pyridazin-6-ylamino)ethanol

Prepared from 3-bromo-6-chloroimidazo[1,2-b]pyridazine and 2-aminoethanol according to general procedure 1 providing the intermediate (78 mg, 32%) as a white solid: $R_f$=0.41 (CH$_2$Cl$_2$/MeOH/NH$_4$OH, 160:18:2); $^1$H NMR (500 MHz, CD$_3$OD) δ 7.55 (d, J=9.7 Hz, 1H), 7.40 (s, 1H), 6.73 (d, J=9.7 Hz, 1H), 3.80 (t, J=5.7 Hz, 2H), 3.52 (t, J=5.7 Hz, 2H); ES-MS: (M+H)=257, 259 m/z.

Step B: Prepared from the product of step A and (E)-1-hexeneboronic acid according to general procedure 2. The free-base was converted to the HCl salt with 2N HCl in Et$_2$O to provide the title compound (45 mg, 53%) as a white solid; $^1$H NMR (500 MHz, CD$_3$OD) δ 7.91 (s, 1H), 7.88 (d, J=9.8 Hz, 1H), 7.22 (d, J=9.8 Hz, 1H), 6.88 (dt, J=7.0, 16.2 Hz, 1H), 6.67 (d, J=16.2 Hz, 1H), 3.81 (t, J=5.7 Hz, 2H), 3.55 (t, J=5.7 Hz, 2H), 2.36-2.32 (m, 2H), 1.55-1.49 (m, 2H), 1.46-1.40 (m, 2H), 0.96 (t, J=7.3 Hz, 3H); $^{13}$C NMR (125 MHz, CD$_3$OD) δ 157.3, 139.2, 133.2, 130.2, 121.0, 120.8, 117.6, 114.2, 60.5, 45.0, 34.3, 32.3, 23.3, 14.3; HPLC $t_R$=10.8 min (Luna), 98.8%; ES-MS: (M+H)=261 m/z.

Example 43

(E)-3-(Hex-1-enyl)-N-(pyridin-4-ylmethyl)imidazo[1,2-b]pyridazin-6-amine

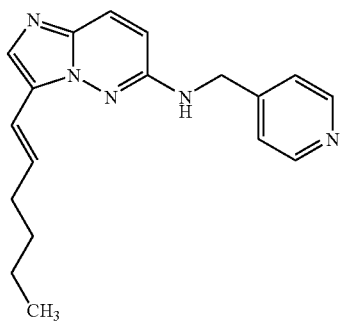

Step A: 3-Bromo-N-(pyridin-4-ylmethyl)imidazo[1,2-b]pyridazin-6-amine

Prepared from 3-bromo-6-chloroimidazo[1,2-b]pyridazine and pyridin-4-ylmethanamine according to general procedure 1 providing the intermediate (94 mg, 84%) as a yellow solid: $R_f$=0.28 (CH$_2$Cl$_2$/MeOH/NH$_4$OH, 160:18:2); $^1$H NMR (500 MHz, CD$_3$OD) δ 8.45-8.46 (m, 2H), 7.60 (d, J=9.7 Hz, 1H), 7.51-7.50 (m, 2H), 7.39 (s, 1H), 6.79 (d, J=9.7 Hz, 1H), 4.61 (s, 2H); ES-MS: (M+H)=304, 306 m/z.

Step B: Prepared from the product of step A and (E)-1-hexeneboronic acid according to general procedure 2 providing the title compound (47 mg, 53%) as a brown solid; $^1$H NMR (500 MHz, CD$_3$OD) δ 8.46-8.44 (m, 2H), 7.61 (d, J=9.1 Hz, 1H), 7.46 (d, J=7.1 Hz, 2H), 7.38 (s, 1H), 6.75 (d, J=9.7 Hz, 1H), 6.56-6.37 (m, 2H), 4.62 (s, 2H), 2.18-2.11 (q, J=6.5 Hz, 2H), 1.39-1.28 (m, 4H), 0.92 (t, J=7.1 Hz, 3H); $^{13}$C NMR (125 MHz, CD$_3$OD) δ 154.8, 152.0, 150.0, 138.0, 133.1, 129.4, 128.6, 125.9, 123.9, 116.6, 113.0, 45.5, 34.3, 32.7, 23.3, 14.3; HPLC $t_R$=10.9 min (Luna), 97.4%; ES-MS: (M+H)=308 m/z.

Example 44

(E)-3-(Hex-1-enyl)-N-((5-methylpyrazin-2-yl)methyl)imidazo[1,2-b]pyridazin-6-amine

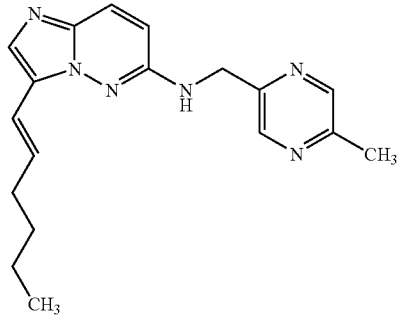

Step A: 3-Bromo-N-((5-methylpyrazin-2-yl)methyl)imidazo[1,2-b]pyridazin-6-amine

Prepared from 3-bromo-6-chloroimidazo[1,2-b]pyridazine and (5-methylpyrazin-2-yl)methanamine according to general procedure 1 providing the intermediate (64 mg, 34%) as a yellow solid: $R_f$=0.67 (CH$_2$Cl$_2$/MeOH/NH$_4$OH, 160:18:2); $^1$H NMR (500 MHz, CD$_3$OD) δ 8.69 (s, 1H), 8.47 (s, 1H), 7.60 (d, J=9.7 Hz, 1H), 7.39 (s, 1H), 6.79 (d, J=9.7 Hz, 1H), 4.66 (s, 2H), 2.53 (s, 3H); ES-MS: (M+H)=319, 321 m/z.

Step B: Prepared from the product of step A and (E)-1-hexeneboronic acid according to general procedure 2 providing the title compound (20 mg, 40%) as a brown solid; $^1$H NMR (500 MHz, CD$_3$OD) δ 8.55 (s, 1H), 8.48 (s, 1H), 7.60 (d, J=9.5 Hz, 1H), 7.39 (s, 1H), 6.75 (d, J=9.5 Hz, 1H), 6.51-6.40 (m, 2H), 4.67 (s, 2H), 2.52 (s, 3H), 2.20-2.15 (m, 2H), 1.42-1.34 (m, 4H), 0.94 (t, J=7.0 Hz, 3H); $^{13}$C NMR (125 MHz, CD$_3$OD) δ 154.8, 153.4, 153.1, 144.9, 143.4, 137.9, 133.2, 129.3, 128.6, 126.0, 116.6, 113.1, 45.9, 34.4, 32.8, 23.4, 20.9, 14.3; HPLC $t_R$=14.6 min (Luna), 98.1%; ES-MS: (M+H)=323 m/z.

Example 45

(E)-3-(Hex-1-enyl)-N-(pyridin-3-ylmethyl)imidazo[1,2-b]pyridazin-6-amine

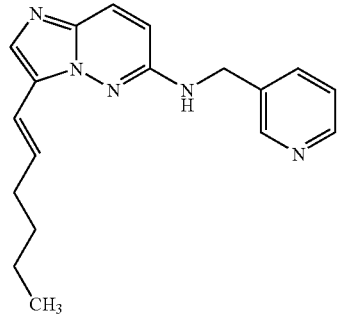

Step A: 3-Bromo-N-(pyridin-3-ylmethyl)imidazo[1,2-b]pyridazin-6-amine

Prepared from 3-bromo-6-chloroimidazo[1,2-b]pyridazine and pyridin-3-ylmethanamine according to general procedure 1 providing the intermediate (88 mg, 45%) as a white solid: $R_f$=0.66 (CH$_2$Cl$_2$/MeOH/NH$_4$OH, 160:18:2); $^1$H NMR (500 MHz, CD$_3$OD) δ 8.70 (d, J=1.9 Hz, 1H), 7.99-7.97 (m, 1H), 7.85-7.82 (m, 1H), 7.59 (d, J=9.7 Hz, 1H), 7.40 (s, 1H), 6.73 (d, J=9.7 Hz, 1H), 4.57 (s, 2H); ES-MS: (M+H)=304, 306 m/z.

Step B: Prepared from the product of step A and (E)-1-hexeneboronic acid according to general procedure 2 providing the title compound (75 mg, 50%) as a brown solid; $^1$H NMR (300 MHz, CD$_3$OD) δ 8.60 (s, 1H), 8.42-8.40 (m, 1H), 7.91 (d, J=7.8 Hz, 1H), 7.57 (d, J=9.7 Hz, 1H), 7.41-7.37 (m, 2H), 6.71-6.47 (m, 3H), 4.60 (s, 2H), 2.24-2.18 (m, 2H), 1.44-1.32 (m, 4H), 0.93 (t, J=7.0 Hz, 3H); $^{13}$C NMR (75 MHz, CD$_3$OD) δ 154.8, 149.5, 148.6, 137.9, 137.5, 137.4, 133.2, 129.1, 128.7, 125.9, 125.2, 116.7, 113.2, 43.9, 34.4, 32.8, 23.3, 14.4; HPLC t$_R$=11.4 min (Luna), 96.0%; ES-MS: (M+H)=308 m/z.

Example 46

(E)-N$^1$-(3-(Hex-1-enyl)imidazo[1,2-b]pyridazin-6-yl)-N$^4$,N$^4$-dimethylbutane-1,4-diamine

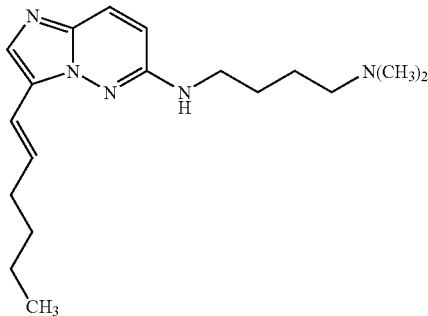

Step A: N$^1$-(3-Bromoimidazo[1,2-b]pyridazin-6-yl)-N$^4$,N$^4$-dimethylbutane-1,4-diamine Prepared from 3-bromo-6-chloroimidazo[1,2-b]pyridazine and N$^1$,N$^1$-dimethylbutane-1,4-diamine according to general procedure 1 providing the intermediate (300 mg, 74%) as a yellow oil: R$_f$=0.40 (CH$_2$Cl$_2$/MeOH/NH$_4$OH, 160:18:2); $^1$H NMR (500 MHz, CDCl$_3$) δ 7.53 (d, J=9.6 Hz, 1H), 7.45 (s, 1H), 6.38 (d, J=9.6 Hz, 1H), 6.07 (brs, 1H), 3.40 (quart, J=5.2 Hz, 2H), 2.34 (t, J=6.8 Hz, 2H), 2.25 (s, 6H), 1.76 (quin, J=6.6 Hz, 2H), 1.64 (quin, J=6.8 Hz, 2H); ES-MS: (M+H)=312, 314 m/z.

Step B: Prepared from the product of step A and (E)-1-hexeneboronic acid according to general procedure 2 providing the title compound (51 mg, 42%) as a brown solid; $^1$H NMR (300 MHz, CDCl$_3$) δ 7.54 (d, J=9.5 Hz, 1H), 7.49 (s, 1H), 6.72-6.58 (m, 2H), 6.32 (d, J=9.5 Hz, 1H), 5.60 (br, 1H), 3.39 (q, J=6.2 Hz, 2H), 2.38 (t, J=6.7 Hz, 1H), 2.31-2.22 (m, 8H), 1.78-1.72 (m, 2H), 1.69-1.63 (m, 2H), 1.52-1.36 (m, 4H), 0.94 (t, J=7.2 Hz, 3H); $^{13}$C NMR (75 MHz, CDCl$_3$) δ 153.3, 136.9, 131.4, 129.4, 127.2, 125.7, 115.9, 110.5, 59.2, 45.1, 41.8, 33.4, 31.7, 26.9, 25.4, 22.3, 13.9; HPLC t$_R$=11.4 min (Luna), 96.8%; ES-MS: (M+H)=316 m/z.

Example 47

(E)-3-(Hex-1-enyl)-N-(3-(pyrrolidin-1-yl)propyl)imidazo[1,2-b]pyridazin-6-amine dihydrochloride

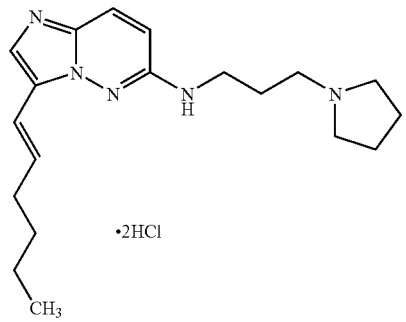

Step A: 3-Bromo-N-(3-(pyrrolidin-1-yl)propyl)imidazo[1,2-b]pyridazin-6-amine

Prepared from 3-bromo-6-chloroimidazo[1,2-b]pyridazine and 3-(pyrrolidin-1-yl)propan-1-amine according to general procedure 1 providing the intermediate (227 mg, 81%) as a clear oil; $^1$H NMR (500 MHz, CDCl$_3$) δ 7.53 (d, J=9.6 Hz, 1H), 7.44 (s, 1H), 6.40 (brs, 1H), 6.35 (d, J=9.6 Hz, 1H), 3.52 (quart, J=5.2 Hz, 2H), 2.67 (t, J=6.2 Hz, 2H), 2.57-2.54 (m, 4H), 1.86 (quin, J=6.3 Hz, 2H), 1.84-1.78 (m, 4H); ES-MS: (M+H)=324, 326 m/z.

Step B: Prepared from the product of step A and (E)-1-hexeneboronic acid according to general procedure 2. The free-base was converted to the dihydrochloride salt with 2N HCl in Et$_2$O to provide the title compound (59 mg, 36%) as a brown solid; $^1$H NMR (500 MHz, CD$_3$OD) δ 7.97 (s, 1H), 7.92 (d, J=9.9 Hz, 1H), 7.23 (d, J=9.9 Hz, 1H), 6.87-6.85 (m, 1H), 6.72-6.69 (m, 1H), 3.70-3.66 (m, 2H), 3.56 (t, J=6.7 Hz, 2H), 3.37-3.34 (m, 2H), 3.13-3.08 (m, 2H), 2.37-2.33 (m, 2H), 2.22-2.13 (m, 4H), 2.06-2.02 (m, 2H), 1.56-1.50 (m, 2H), 1.47-1.41 (m, 2H), 0.97 (t, J=7.3 Hz, 3H); $^{13}$C NMR (125 MHz, CD$_3$OD) δ 157.1, 139.2, 133.2, 130.4, 121.3, 120.7, 117.6, 114.2, 55.3, 54.2, 39.7, 34.3, 32.3, 26.0, 24.1, 23.3, 14.3; HPLC t$_R$=12.3 min (Luna), 97.6%; ES-MS: (M+H)=328 m/z.

Example 48

(E)-N$^1$-(3-(Hex-1-enyl)imidazo[1,2-b]pyridazin-6-yl)propane-1,3-diamine

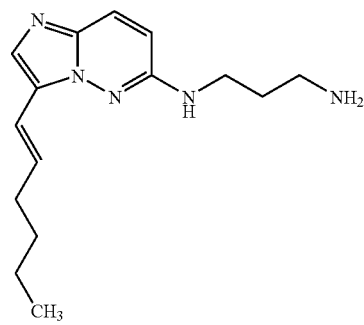

Step A: tert-Butyl 3-(3-bromoimidazo[1,2-b]py-ridazin-6-ylamino)propylcarbamate Prepared from 3-bromo-6-chloroimidazo[1,2-b]py-ridazine and tert-butyl 3-aminopropylcarbamate according to general procedure 1 providing the intermediate (300 mg, 63%) as a yellow oil: $R_f$=0.65 (CH$_2$Cl$_2$/MeOH/NH$_4$OH, 160:18:2); $^1$H NMR (500 MHz, CDCl$_3$) δ 7.56 (d, J=9.6 Hz, 1H), 7.46 (s, 1H), 6.46 (d, J=9.6 Hz, 1H), 5.13-5.10 (m, 2H), 3.53 (quart, J=6.2 Hz, 2H), 3.27-3.23 (m, 2H), 1.84-1.79 (m, 2H), 1.46 (s, 9H); ES-MS: (M+H)=370, 372 m/z.

Step B: (E)-tert-Butyl 3-(3-(hex-1-enyl)imidazo[1,2-b]pyridazin-6-ylamino)propylcarbamate Prepared from the product from step A and (E)-1-hex-eneboronic acid according to general procedure 2 providing the crude Boc-protected olefin (122 mg, 96%) as a brown oil: $R_f$=0.71 (CH$_2$Cl$_2$/MeOH/NH$_4$OH, 160:18:2); $^1$H NMR (500 MHz, CD$_3$OD) δ 7.78 (d, J=9.7 Hz, 1H), 7.54 (s, 1H), 6.64-6.40 (m, 3H), 3.47 (q, J=6.3 Hz, 2H), 3.29-3.23 (m, 2H), 2.36-2.30 (m, 2H), 1.84-1.81 (m, 2H), 1.50-1.42 (m, 11H), 1.40-1.48 (m, 2H), 0.93 (t, J=7.3 Hz, 3H).

Step C: The product from step B was stirred in TFA (3 mL) for 3 h. The reaction mixture was concentrated and partitioned between ethyl acetate and saturated sodium carbonate solution and the organic layer removed and concentrated. Purification by column chromatography (12 g ISCO column eluting with methylene chloride and methanol/ammonia mixture (10:1); gradient 100% methylene chloride to 70% methylene chloride over 30 min at 25 mL/min) provided the title compound (26 mg, 29%) as a yellow solid; $^1$H NMR (500 MHz, CD$_3$OD) δ 7.56 (d, J=9.6 Hz, 1H), 7.45 (s, 1H), 6.69-6.61 (m, 3H), 3.51 (t, J=6.4 Hz, 2H), 3.07 (t, J=7.4 Hz, 2H), 2.29-2.27 (m, 2H), 2.06 (m, 2H), 1.50-1.43 (m, 4H), 0.96 (t, J=7.1 Hz, 3H); $^{13}$C NMR (125 MHz, CD$_3$OD) δ 155.3, 133.2, 128.8, 128.6, 125.7, 116.7, 113.6, 39.5, 39.0, 34.4, 32.9, 27.9, 23.4, 14.3 (one aromatic carbon overlapping); HPLC $t_R$=10.9 min (Luna), 94.7%; ES-MS: (M+H)=274 m/z.

Example 49

Anti-(E)-4-(3-(Hex-1-enyl)imidazo[1,2-b]pyridazin-6-ylamino)cyclohexanol

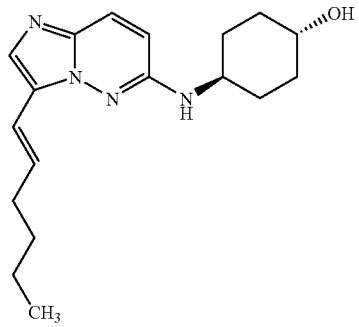

Example 50

Syn-(E)-4-(3-(Hex-1-enyl)imidazo[1,2-b]pyridazin-6-ylamino)cyclohexanol hydrochloride

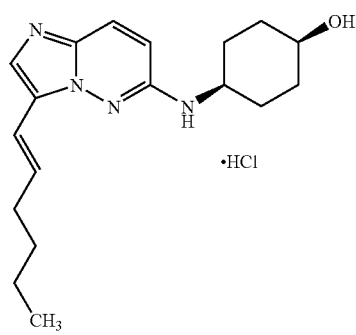

Step A: 4-(3-Bromoimidazo[1,2-b]pyridazin-6-ylamino)cyclohexanol

Prepared from 3-bromo-6-chloroimidazo[1,2-b]py-ridazine and 4-aminocyclohexan-1-ol (mixture of syn and anti isomers) according to general procedure 1 providing the intermediate (215 mg, 32%) as a yellow oil (syn and anti isomers not separated): $R_f$=0.58 (CH$_2$Cl$_2$/MeOH/NH$_4$OH, 160:18:2); ES-MS: (M+H)=311, 313 m/z.

Step B: Prepared from the product of step A and (E)-1-hexeneboronic acid according to general procedure 2 providing the title compound as a mixture of syn and anti-isiomers, that were separated by semi-prep HPLC.

The anti isomer (example 49) was isolated as a white solid (22 mg, 10%); $^1$H NMR (500 MHz, CD$_3$OD) δ 7.51 (d, J=9.7 Hz, 1H), 7.38 (s, 1H), 6.86-6.80 (dt, J=7.1, 16.0 Hz, 1H), 6.66 (d, J=9.7 Hz, 1H), 6.58 (d, J=16.0 Hz, 1H), 3.87-3.80 (m, 2H), 2.29-2.25 (m, 2H), 1.86-1.67 (m, 8H), 1.53-1.38 (m, 4H), 0.97 (t, J=7.3 Hz, 3H); $^{13}$C NMR (125 MHz, CD$_3$OD) δ 154.6, 137.6, 133.2, 128.4, 125.0, 116.8, 115.0, 114.2, 67.6, 49.1, 34.4, 32.9, 32.0, 27.8, 23.2, 14.3; HPLC $t_R$=17.4 min (Luna), 97.8%; ES-MS: (M+H)=315 m/z.

The syn-isomer (example 50) was converted to the HCl salt with 2N HCl in Et$_2$O to provide the title compound (22 mg, 8%) as a solid; $^1$H NMR (500 MHz, CD$_3$OD) δ 7.86-7.83 (m, 2H), 7.13 (d, J=9.8 Hz, 1H), 7.01 (dt, J=7.0, 16.1 Hz, 1H), 6.61 (dd, J=1.1, 16.1 Hz, 1H), 3.74-3.71 (m, J=Hz, 1H), 3.64-3.61 (m, 1H), 2.37-2.33 (m, 2H), 2.22-2.18 (m, 2H), 2.05-2.03 (m, 2H), 1.57-1.51 (m, 2H), 1.48-1.35 (m, 6H), 0.96 (t, J=7.4 Hz, 3H); $^{13}$C NMR (125 MHz, CD$_3$OD) δ 156.4, 139.0, 133.2, 129.8, 121.0, 120.7, 118.1, 114.5, 70.5, 51.4, 34.8, 34.0, 32.3, 30.7, 23.3, 14.3; HPLC $t_R$=16.1 min (Luna), 96.4%; ES-MS: (M+H)=315 m/z.

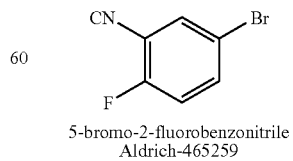

5-bromo-2-fluorobenzonitrile
Aldrich-465259

6-chloro-pyridazinamine
Aldrich-R262277

↓ ↓

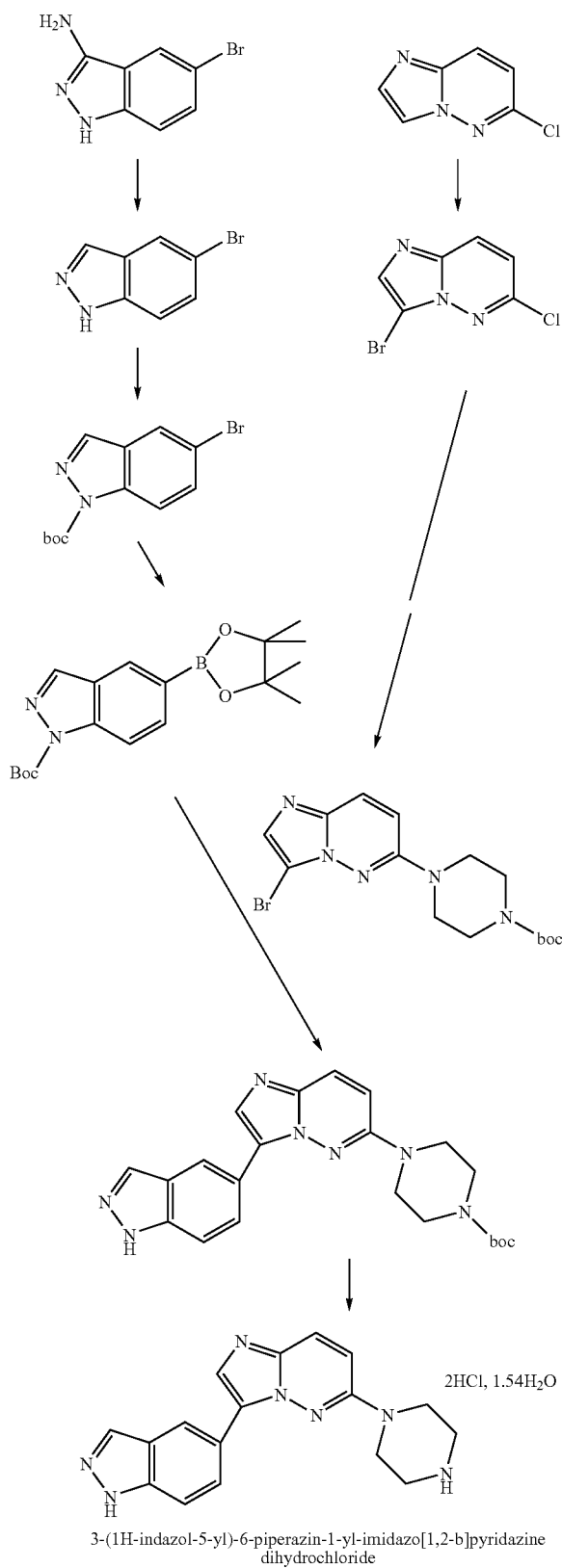

3-(1H-indazol-5-yl)-6-piperazin-1-yl-imidazo[1,2-b]pyridazine dihydrochloride

Example 51

3-(1H-Indazol-5-yl)-6-piperazin-1-yl-imidazo[1,2-b]pyridazine dihydrochloride Step A: 3-Amino-5-bromo-indazole A mixture of 5-bromo-2-fluorobenzonitrile (5.00 g, 25 mmol) and hydrazine hydrate (10 mL) was heated at reflux for two hours and then it was allowed to stand at room temperature for two days. The reaction was treated with water (50 mL) and the solids were collected by filtration to give 3-Amino-5-bromo-indazole as a white solid (4.82 g, 91%): mp 165-175° C.; MS [M+H]$^+$ 212, 214.

Step B: 5-Bromo-indazole

A mixture of 3-amino-5-bromo-indazole, (4.60 g, 22 mmol) and ethanol (50 mL) was treated with hypophosphorous acid (50% aqueous solution, 9.6 ml, 87 mmol) and cooled to 0° C. To the reaction mixture was added isobutyl nitrite (2.6 mL, 22 mmol). The mixture was warmed to room temperature and the yellow suspension was stirred for two hours. The resulting brown suspension was treated with isobutyl nitrite (1 mL) and stirred at room temperature for one hour. The reaction was quenched with brine (100 mL) and the mixture extracted with ethyl acetate (2×100 mL). The combined organic layers were dried over magnesium sulfate, filtered and evaporated to a brown oil which was purified by chromatography using silica gel and hexane/ethyl acetate to give 5-bromo-indazole as a tan solid (1.74 g, 40%): mp 122-124° C.; MS [M+H]$^+$ 195, 197.

Step C: 1-(tert-Butoxycarbonyl)-5-bromo-indazole

A mixture of 5-bromo-indazole, (1.80 g, 9.2 mmol) and THF (20 mL) at 0° C. was treated with sodium hydride (60% in oil, 0.4 g, 10 mmol) and stirred for 10 minutes. Then the reaction was treated with di-tert-butyl-dicarbonate (2.01 g, 9.2 mmol). The pasty mixture was diluted with THF (20 mL), warmed to room temperature and stirred for 2 hours. At this point the reaction was quenched with a saturated aqueous solution of sodium bicarbonate (100 mL) and the mixture was extracted with ethyl acetate (2×100 mL). The combined organic layers were dried over magnesium sulfate, filtered and evaporated to a tan oil (2.16 g). This oil was purified by chromatography using silica gel and hexane/ethyl acetate gradient to give 1-(tert-butoxycarbonyl)-5-bromo-indazole as a yellow oil (1.83 g, 67%), which was about 90% pure by $^1$H NMR (CDCl$_3$) δ 8.11 (s, 1H), 8.10 and 7.61 (ABq, 1H, J=11 Hz and 2 Hz), 7.88 (dd, 1H, J=2Hz), 1.73 (s, 3H).

Step D: 6-Chloro-imidazo[1,2-b]pyridazine

A mixture of 6-chloro-pyridazinamine (5.00 g, 38 mmol) in 1-butanol (5 mL) was treated with chloroacetaldehyde (50% in water, 5.0 mL, 38 mmol) and the tan suspension was refluxed two hours and to give a dark solution. The reaction mixture was cooled to room temperature and the solid was collected by filtration and washed with methanol to afford a brown solid (3.04 g); evaporation of the filtrate gave additional product (4.60 g). The solids were combined (7.64 g) and used in the next reaction without further purification: MS [M+H]+ 154.

Step E:
3-Bromo-6-chloro-1-yl-imidazo[1,2-b]pyridazine

Bromine (1.74 mL, 34 mmol) was added dropwise to an ice cold mixture of acetic acid (2 mL) and 6-Chloro-imidazo[1,2-b]pyridazine (6.72 g, 34 mmol) in methanol (300 mL). After the addition was completed the mixture was allowed to warm to room temperature and then stirred for one hour. The reaction was treated with saturated aqueous sodium bisulfite (100 mL) and the volatiles were removed under vacuum followed by the addition of ethyl acetate (150 mL). The solids were collected by filtration and dried under vacuum to give 3-bromo-6-chloro-1-yl-imidazo[1,2-b]pyridazine as a pinkish solid (3.20 g): mp 157° C. The organic layer of the filtrate was dried over anhydrous magnesium sulfate, filtered and evaporated to give a second crop of 3-bromo-6-chloro-1-yl-imidazo[1,2-b]pyridazine as a yellow solid. The combined solids were 6.71 g (86%).

Method 2: A mixture of 6-chloro-imidazo[1,2-b]pyridazine (0.40 g, 2.6 mmol) and bromine (0.12 mL, 2.3 mmol) in methanol (20 mL) was stirred at room temperature. Evaporation of the reaction mixture gave 3-bromo-6-chloro-1-yl-imidazo[1,2-b]pyridazine as a yellow solid (0.69 g); this material was used in the next reaction without further purification: LC/MS [M+H]+ 232, 234.

Step F: 4-(3-Bromo-imidazo[1,2-b]pyridazine-6-yl)-piperazine-1-carboxylic acid tert-butyl ester To a mixture of 3-bromo-6-chloro-1-yl-imidazo[1,2-b]pyridazine (1.00 g, 4.3 mmol) in 1,2-dimethoxy ethane (1 mL) was added diisopropyl ethyl amine (0.5 mL) and 1-BOC-piperazine (2.41 g, 13 mmol). The mixture was degassed (4 cycles of vacuum and nitrogen) and heated at 120° C. for 27 hours. The reaction mixture was cooled to room temperature, treated with saturated aqueous sodium bicarbonate (100 mL) and extracted with ethyl acetate (2×100 mL). The organic layers were combined and dried with magnesium sulfate, filtered and evaporated to a residue, which was purified by chromatography on silica gel; elution with a gradient of hexane/ethyl acetate gave 4-(3-bromo-imidazo[1,2-b]pyridazine-6-yl)-piperazine-1-carboxylic acid tert-butyl ester as an off-white solid (1.01 g, 83%): mp 176-9° C.; LC/MS [M+H]+ 382, 384.

Step G: 3-(1H-Indazol-5-yl)-6-piperazin-1-yl-imidazo[1,2-b]pyridazine dihydrochloride To a mixture of 1-BOC-5-bromo-indazole (0.4 g, 1.3 mmol) in DMF (10 mL) at room temperature, under nitrogen was added potassium acetate (0.40 g, 4 mmol), bis(pinacolato)diboron (0.38 g, 1.5 mmol) and Pd(dppf)Cl$_2$CH$_2$Cl$_2$ (80 mg, 1.1 mmol). The mixture was degassed with 4 cycles of vacuum and nitrogen and heated at 80° C. for two hours and then cooled to room temperature to give an intermediate (5-(4,4,5,5-tetramethyl-1,3,2-dioxaborolan-2-yl)-indazole-1-carboxylic acid benzyl ester). To this mixture was added 3-bromo-6-(4-tert-butoxycarbonyl)piperazin-1-yl-imidazo[1,2-b]pyridazine (0.52 g, 1.3 mmol), potassium carbonate (0.40 g), water (2 mL), and then was degassed and heated at 100° C. for 2 hours and 120° C. for one hour. The reaction mixture was cooled to room temperature and treated with saturated aqueous sodium bicarbonate (100 mL) and extracted with ethyl acetate (3×100 mL). The organic layers were combined, dried with magnesium sulfate, filtered and evaporated to a residue that was purified by chromatography with silica gel and ethyl acetate. The purified intermediate (0.15 g, MS m/z 420) was treated with methanol (5 ml) and aqueous HCl (20%, 5 mL) at room temperature overnight. Evaporation of the mixture gave 3-(1H-indazol-5-yl)-6-piperazin-1-yl-imidazo[1,2-b]pyridazine dihydrochloride, as a white solid (0.13 g, 27%): mp decomposed above 315° C., MS [M+H]+ m/z 320. Anal. (C$_{18}$H$_{17}$N$_7$.2HCl .1.54H$_2$O) C, H, N.

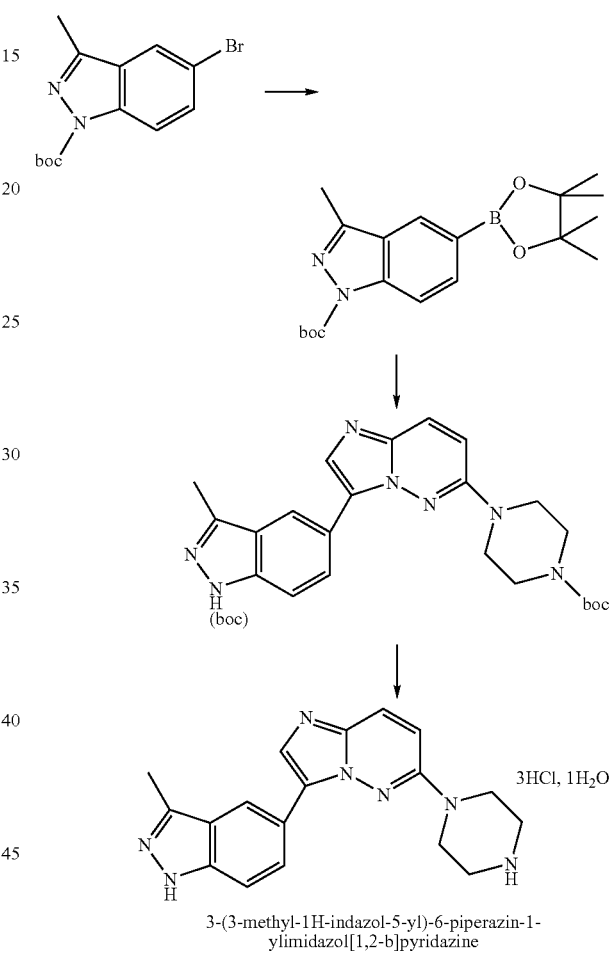

3-(3-methyl-1H-indazol-5-yl)-6-piperazin-1-ylimidazol[1,2-b]pyridazine

Example 52

3-(3-Methyl-1H-indazol-5-yl)-6-piperazin-1-yl-imidazo[1,2-b]pyridazine trihydrochloride A solution of 1-BOC-3-methyl-5-bromo-indazole (0.42 g, 1.35 mmol) in DMF (10 mL) at room temperature, under nitrogen and treated with potassium acetate (0.40 g, 0.004 mol), bis(pinacolato)diboron (0.38 g, 1.5 mmol) and Pd(dppf)Cl$_2$.CH$_2$Cl$_2$ (80 mg, 0.1 mmol). This suspension was degassed with four cycles of vacuum and nitrogen. The suspension was heated at 80° C. for two hours and then cooled to room temperature. The suspension was treated with 3-bromo-6-(4-tert-butoxycarbonyl)piperazin-1-yl-imidazo[1,2-b]pyridazine (0.50 g, 1.3 mmol) and potassium carbonate (0.40 g) and water (2 mL), degassed (vacuum and then nitrogen×4)

and heated at 100° C. for 2 hours. The reaction was cooled to room temperature, quenched with saturated aqueous sodium bicarbonate (150 mL) and extracted with ethyl acetate (3×50 mL). The organic layers were combined, dried with anhydrous magnesium sulfate, filtered and evaporated. After chromatography with silica gel and a gradient of hexane/ethyl acetate a mixture of mono and di-BOC protected material was obtained as shown by MS m/z 434 and 534. This mixture was treated with aqueous HCl (20%, double distilled, 5 mL) at room temperature overnight. Then the reaction was evaporated to give 3-(3-methyl-1H-indazol-5-yl)-6-piperazin-1-yl-imidazo[1,2-b]pyridazine trihydrochloride as an off white solid (0.27 g, 43%), decomposed above 316° C., MS [M+H]$^+$ 334. Anal. ($C_{18}H_{19}N_7$.3HCl .1.0$H_2O$), C, H, N, Cl.

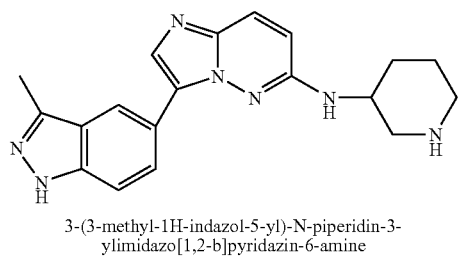

3-(3-methyl-1H-indazol-5-yl)-N-piperidin-3-ylimidazo[1,2-b]pyridazin-6-amine

Example 53

[3-(3-methyl-1H-indazol-5-yl)-imidazo[1,2-b]pyridazine-6-yl]-piperidin-3-yl-amine trihydrochloride Step A 3-(3-Bromo-imidazo[1,2-b]pyridazine-6-ylamino)-piperidin-1-carboxylic acid tert-butyl ester was prepared in a manner similar to the procedure in Step F of Example 51 with (±)-3-amino-1-N-Boc-piperidine (1.73 g, 8.6 mmol) and 3-bromo-6-chloro-1-yl-imidazo[1,2-b]pyridazine (0.5 g, 2.16 mmol) in a sealed tube, degassed (with cycles of vacuum and nitrogen×4) and heated to melt the reagents overnight. Chromatography with silica gel and ethyl acetate/dichloromethane gave 3-(3-bromo-imidazo[1,2-b]pyridazine-6-ylamino)-piperidin-1-carboxylic acid as a yellow oil, 0.31 g (36%), MS [M+H]$^+$ m/z 396 and 398.

Step B [3-(3-methyl-1H-indazol-5-yl)-imidazo[1,2-b]pyridazine-6-yl]-piperidin-3-yl-amine trihydrochloride A solution of 1-BOC-3-methyl-5-bromo-indazole (0.24 g, 0.76 mmol), in DMF (10 mL) at room temperature, under nitrogen and treated with potassium acetate (0.40 g, 4 mmol), bis(pinacolato)diboron (0.38 g, 1.5 mmol) and Pd(dppf)Cl$_2$.CH$_2$Cl$_2$ (80 mg, 0.1 mmol). This suspension was degassed with four cycles of vacuum and nitrogen. The suspension was heated at 80° C. for two hours and then cooled to room temperature. The suspension was treated with 3-(3-bromo-imidazo[1,2-b]pyridazine-6-yl-amino)-piperidine-1-carboxylic acid tert-butyl ester (0.31 g, 0.76 mmol) and potassium carbonate (0.40 g) and water (2 mL), degassed (vacuum and then nitrogen×4) and heated at 100° C. for 2 hours. The reaction mixture was cooled to room temperature, quenched with saturated aqueous sodium bicarbonate (100 mL) and extracted with ethyl acetate (3×50 mL). The organic layers were combined, dried with anhydrous magnesium sulfate, filtered and evaporated. After chromatography with silica gel and a gradient of hexane/ethyl acetate a mixture of mono and di-BOC protected material was obtained as shown by MS m/z 448 and 548. This mixture was treated with aqueous HCl (20%, double distilled, 5 mL) at room temperature overnight. Then the reaction mixture was evaporated to give [3-(3-methyl-1H-indazol-5-yl)-imidazo[1,2-b]pyridazine-6-yl]-piperidin-3-yl-amine trihydrochloride as an yellow solid (0.12 g, 34%); this material was purified by reversed phase chromatography (20.9 mg): mp decomposed above 250° C.; MS [M+H]$^+$ m/z 348. Anal. ($C_{19}H_{21}N_7$.3HCl.1.08$H_2O$), C, H, N.

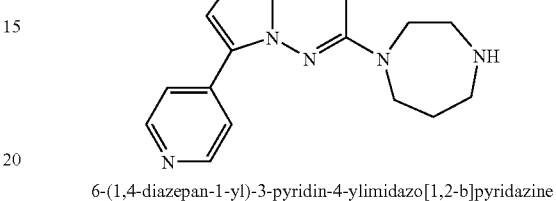

6-(1,4-diazepan-1-yl)-3-pyridin-4-ylimidazo[1,2-b]pyridazine

Example 54

6-(1,4-Diazepan-1-yl)-3-pyridin-4-yl-imidazo [1,2-b]pyridazine hydrochloride

Step A 4-(3-Bromo-imidazo[1,2-b]pyridazine-6-yl)-(1,4-Diazepan-1-yl)-carboxylic acid tert-butyl ester was prepared in a manner similar to the procedure in Step F of Example 51 with 1-Boc-4-homopiperazine (2.0 mL, 10.2 mmol) and 5 (0.4 g, 1.72 mmol) in a sealed tube with ethanol (10 mL), degassed (with cycles of vacuum and nitrogen×4) and heated to melt the suspension into a solution at 120-130° C. overnight. Chromatography with silica gel and dichloromethane/ethyl acetate gave 4-(3-bromo-imidazo[1,2-b]pyridazine-6-yl)-(1,4-Diazepan-1-yl)-carboxylic acid as a colorless oil, 0.53 g (78%), MS [M+H]$^+$ m/z 396 and 398. 6-(1,4-Diazepan-1-yl)-3-pyridin-4-yl-imidazo[1,2-b]pyridazine hydrochloride, A solution 4-(3-bromo-imidazo[1,2-b]pyridazine-6-yl)-(1,4-Diazepan-1-yl)-carboxylic acid tert-butyl ester (0.47 g, 1.2 mmol), in DMF (8 mL) at room temperature under nitrogen was treated with Pd(dppf)Cl$_2$.CH$_2$Cl$_2$ (200 mg, 0.24 mmol) and stirred at room temperature for 10 minutes. This suspension was treated with potassium carbonate (0.40 g), water (2 mL) and 4-pyridine boronic acid (0.29 g, 1.8 mmol) and degassed with four cycles of vacuum and nitrogen. The suspension was heated at 130° C. for 30 minutes. Then the reaction was cooled to room temperature and evaporated to give a dark solid. After chromatography with silica gel and a gradient of ethyl acetate/dichloromethane a boc-protected derivative was obtained as a tan foam, 0.28 g, MS [M+H]$^+$ 395. This material was dissolved in ethyl acetate (50 mL), washed with aqueous saturated sodium bicarbonate (100 mL), dried with anhydrous magnesium sulfate, treated with fluorasil (10 mg) and decolorizing charcoal (10 mg), filtered and evaporated to give a tan oil, 0.26 g. This material was dissolved in methanol and treated with aqueous HCl (20%, double distilled) at room temperature overnight. The reaction mixture was evaporated to a yellow solid (0.25 g, 55%): mp decomposed above 226° C.; MS [M+H]$^+$ mz 295.

Preparation 1

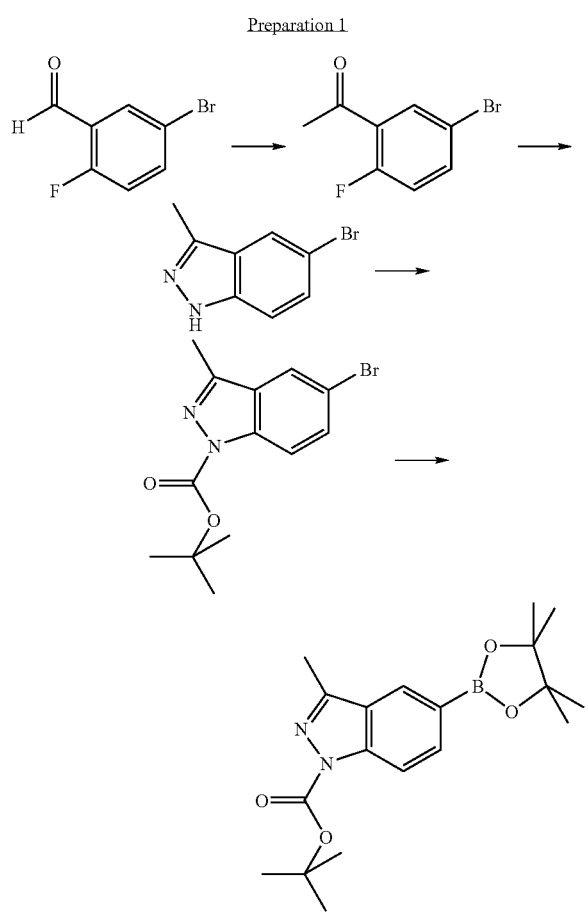

Preparation 1. Preparation of 3-Methyl-5-(4,4,5,5-tetramethyl-1,3,2-dioxaborolan-2-yl)-indazole-1-carboxylic acid tert-butyl ester

Step A: 1-(5-Bromo-2-fluoro-phenyl)-ethanone

To a 0° C. stirred solution of 5-bromo-2 fluoro-benzaldehyde (5.00 g, 24.6 mmol) in anhydrous ether (100 mL) under nitrogen gas was added via syringe MeMgBr (3M solution in ether, 10 mL, 30 mmol) over 3 min. After 30 min, TLC showed the reaction completed. The mixture was poured into a saturated solution of sodium bicarbonate (100 mL), the organic layer was separated and the aqueous layer was extracted with ethyl acetate (100 mL). The combined organic layers were dried over magnesium sulfate, filtered, and concentrated to give a viscous oil. The oil was mixed with acetone (100 mL) and treated with Jones reagent (1.1 M, 40 mL, 1.79 mmol). The mixture was stirred overnight, acetone was evaporated and the residue was extracted with ethyl acetate (60 mL×2). The extracts were washed with water (50 mL) and then a saturated aqueous solution of sodium bicarbonate (50 mL). Evaporation gave the ketone as an oil (4.63 g, 87%) that was used in the next reaction without further purification.

Step B: 5-Bromo-3-methyl-1H-indazole

A mixture of the ketone (0.64 g, 2.95 mmol) from step A in ethylene glycol (5 mL) was placed in a sealed vial and heated at 165° C. overnight (about 15 h). The mixture was mixed with water (50 mL) and extracted with ethyl acetate (50 mL×2). The combined extracts were dried, filtered, and evaporated to give an oil. The oil was purified by chromatography (silica gel, hexane/ethyl acetate 3:1) to give the title compound (0.25 g, 43%) as a yellow solid. LC/MS (+APCI) 211, 213 m/z.

Step C: 5-Bromo-3-methylindazole-1-carboxylic acid tert-butyl ester

To a stirred mixture of indazole from step B (4.06 g, 19.2 mmol), triethylamine (2.32 g, 3.20 mL, 23.0 mmol) in anhydrous THF (80 mL) was added di-tert-butyl-dicarbonate (5.02 g, 23.0 mmol) at ambient temperature, followed by DMAP (cat., about 0.1 g). The reaction was stirred overnight, evaporated to dryness, mixed with a saturated solution of sodium bicarbonate (100 mL) and extracted with ethyl acetate (100 mL×2). The combined extracts were dried, filtered and concentrated to give a solid. Solid from a ethyl acetate/hexane trituration (1:10) was filtered and dried to afford 4.94 g of the desired product. The mother liquid was chromatographed on silica (5% EtOAc/Hex) to give 0.80 g of product (96% total yield).

Step D: 3-Methyl-5-(4,4,5,5-tetramethyl-1,3,2-dioxaborolan-2-yl)-indazole-1-carboxylic acid tert-butyl ester A mixture of the bromide from step C (5.00 g, 16.1 mmol), bis(pinacolato)diboron (4.49 g, 17.7 mmol), potassium acetate (4.73 g, 48.3 mmol), and Pd(dppf)Cl$_2$ (0.66 g, 0.81 mmol) in anhydrous DMF (60 mL) was placed in a vial with rubber-lined screw caps and degassed by three vacuum/nitrogen cycles. The suspension was then heated at 100° C. with stirring under nitrogen for 2 h. The mixture was cooled, mixed with a saturated aqueous solution of sodium bicarbonate (100 mL) and extracted with ethyl acetate (2×150 mL). The crude was chromatographed on silica eluting with a gradient of ethyl acetate/hexane (0% to 15%) to give the desired boronic ester as an oil (5.55 g, 96%). LCMS (+APCI) 499 (M+H).

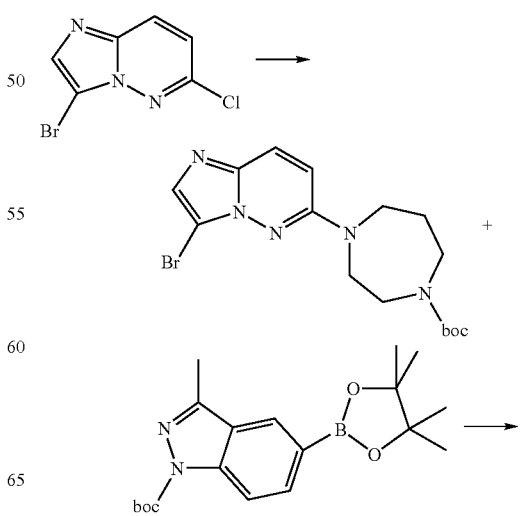

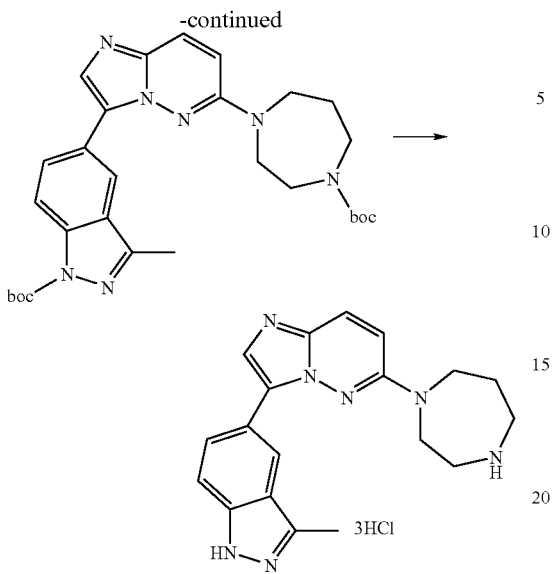

Example 55

3-(3-Methyl-1H-indazol-5-yl)-6-perhydro-1,4-diazepin-1-yl-imidazo[1,2-b]pyridazine trihydrochloride Step A 5-[6-(4-tert-Butoxycarbonyl-perhydro-1,4-diazepin-1-yl)-imidazo[1,2-b]pyridazin-3-yl]-3-methylindazole-1-carboxylic tert-butyl ester A mixture of 4-(3-bromo-imidazo[1,2-b]pyridazine-6-yl)-(1,4-diazepan-1-yl)-carboxylic acid tert-butyl ester (0.50 g, 1.26 mmol), 3-methyl-5-(4,4,5,5-tetramethyl-1,3,2-dioxaborolan-2-yl)-indazole-1-carboxylic acid tert-butyl ester from Preparation 1 (0.46 g, 1.26 mmol), potassium carbonate (powder, 0.52 g, 3.78 mmol), 2N aqueous potassium carbonate (1 mL) and Pd(dppf)Cl$_2$ (0.10 g, 0.13 mmol) in DMF (20 mL) was placed in a vial with rubber-lined screw caps and degassed by three vacuum/nitrogen cycles. The suspension was then heated at 80° C. for 3 h with stirring under nitrogen. The mixture was cooled, mixed with a saturated aqueous solution of sodium bicarbonate (100 mL) and extracted with ethyl acetate (3×100 mL). The crude was chromatographed on silica eluting with a gradient of ethyl acetate/hexane (50% to 100%) and then methanol/ethyl acetate (3% to 7%) to give 0.46 g of an oil. The oil was dissolved in ethyl acetate and precipitated by the addition of hexane (about 10:1). The solid was filtered and dried to give 0.37 g (54%) of the desired compound. LCMS (+APCI) 548 (M+H) and 448 (M+H–100).

Step B: The compound from step A (0.37 g, 0.68 mmol) was mixed with trifluoroacetic acid (8 mL) and stirred for 2 h at ambient temperature. The volatile was removed by evaporation. The residue was dissolved in methanol/water (10:1) and treated with ethanol/HCl (2N, 2 mL). The salt was solidified from methanol and filtered to give a beige solid (0.25 g, 78%). Calculated for C19H21N7.3HCl.H2O: C 48.06, H 5.52, N 20.65. Found: C 48.16, H 5.59, N 20.30. PNMR (DMSO-d6, 323° F.) δ 9.62-9.50 (1.3 H), 8.57 (s, 1H), 8.51 (s, 1H), 8.24 (d, J=10.2 Hz, 1H), 7.94 (dd, J=9.6, 1.5 Hz, 1H), 7.71 (d, H=9.6 Hz, 1H), 7.63 (d, J=8.4 Hz, 1H), 5.90-4.15 (bs, 3.2 H), 4.04 (t, J=5.1Hz, 2H), 3.85 (t, J=5.4 Hz, 2H), 3.34 (m, 2H), 3.21 (m, 2H), 2.55 (s, 3H), 2.18 (m, 2H). CNMR (DMSO-d6, 323° F.) δ 154.72, 141.68, 140.45, 131.75, 128.74, 125.31, 121.87, 121.53, 119.30, 119.07, 11 7.14, 115.66, 110.46, 46.49, 44.22, 444.20, 444.16, 24.13, 11.44.

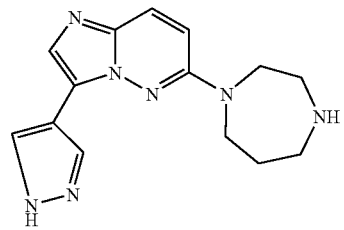

Example 56

6-Perhydro-1,4-diazepin-1-yl-3-(1H-pyrazol-4-yl)-imidazo[1,2-b]pyridazine dihydrochloride Using the procedure in the Example 55 and pyrazole-4-boronic acid pinacol ester the title was prepared. Calculated for C14H17N7.2HCl.1.5H$_2$O.0.1EtOAc: C 44.11, H 5.86, N 25.01. Found: C 44.09, H 5.66, N 24.97.

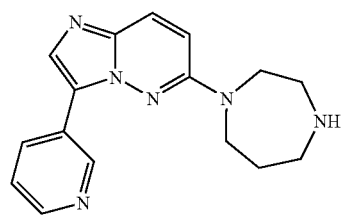

Example 57

6-Perhydro-1,4-diazepin-1-yl-3-pyridin-3-yl-imidazo[1,2-b]pyridazine trihydrochloride Using the procedure in the Example 55 and pyridine-3-boronic acid the title was prepared as beige solid. Calculated for C16H18N6.3HCl.0.2H$_2$O: C 47.18, H 5.30, N 20.63. Found: C 47.20, H 5.27, N 20.53.

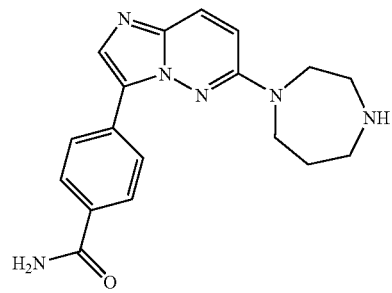

Example 58

4-(6-Perhydro-1,4-diazepin-1-yl-imidazo[1,2-b]pyridazin-3-yl)benzamide dihydrochloride Using the procedure in the Example 55 and (4-aminocarbonylphenyl)boronic acid the title was prepared as an white solid. LCMS (+APCI) 337 (M+H). Calculated for C18H20N6.2HCl.2H$_2$O: C 48.55, H 5.88, N 18.87. Found: C 48.49, H 5.83, N 18.70.

Activity/Efficacy

Method 1

Rho Kinase Assays

The rho kinase assays were performed using a Biomek 2000 Robotic Workstation (Beckman Instruments, Palo Alto, Calif.) in a 96-well plate format. The assay was performed utilizing the IMAP ROCK-I and ROCK-II kits (Molecular Devices, Sunnyvale, Calif.) as follows. Substrate and ATP concentrations used were 200 nM and 10 µM, respectively, while the enzyme concentration was $3.96\times10^{-3}$ units per well. The substrate, enzyme, and ATP dilutions were made with the reaction buffer provided by the vendor. Test compounds were diluted in 10:10 DMSO-ethanol (vol/vol). For the actual assay, the various components were added into black, clear bottom, 96-well plates (Costar, Corning, N.Y.) in a final volume of 20µl per well. After the enzyme reaction (60 min at 23° C.), 60 µl of the binding solution was added per well and incubated for an additional 30 minutes in the dark at 23° C. Fluorescence polarization of the reaction mixtures was then measured on the Analyst™ HT instrument (Molecular Devices, Sunnyvale, Calif.). The data were then analyzed using a non-linear, iterative, sigmoidal-fit computer program purchased from IDBS (Emeryville, Calif.) and as previously described (Sharif et al., *J. Pharmacol. Exp. Ther.*, Vol. 286: 1094-1102, 1998; Sharif et al., *J. Pharmacol. Expt. Ther., Vol.* 293:321-328, 2000; Sharif et al., *J. Ocular Pharmacol. Ther., Vol.* 18:141-162, 2002a; Sharif et al., *J. Pharmac. Pharmacol., Vol.* 54:539-547, 2002b) to generate the inhibition constants for the test compounds.

| Example Number | IC50 (uM) ROCK 1 | IC50 (uM) ROCK 2 |
|---|---|---|
| 1 | 17 | 69 |
| 2 | >100 | >100 |
| 3 | 12 | 56 |
| 4 | >100 | >100 |
| 5 | 9.7 | >100 |
| 6 | 30 | 33 |
| 7 | 35 | 20 |
| 8 | 58 | 65 |
| 9 | 7 | 3.7 |
| 10 | 78 | >100 |
| 11 | 36 | 79 |
| 12 | >100 | 97 |
| 13 | 25 | 17 |
| 14 | 37 | 71 |
| 15 | 67 | 16 |
| 16 | >100 | >100 |
| 17 | 28 | >100 |
| 18 | 43 | 88 |
| 19 | 2.1 | 2 |
| 20 | 55 | >100 |
| 21 | >100 | 200 |
| 22 | 38 | 120 |
| 24 | >100 | >100 |
| 25 | >100 | >100 |
| 26 | 9 | 5.8 |
| 27 | 43 | 88 |
| 28 | >100 | >100 |
| 29 | 42 | 17 |
| 30 | >100 | >100 |
| 31 | >100 | >100 |
| 32 | >100 | >100 |
| 33 | >100 | 13 |
| 34 | >100 | >100 |
| 35 | >100 | >100 |
| 37 | 23 | 13 |
| 38 | 47 | 97 |
| 39 | 1.1 | 0.77 |
| 40 | >100 | >100 |
| 42 | 17 | 34 |
| 43 | 4.3 | 11 |
| 44 | 22 | 34 |
| 45 | 2.3 | 4.7 |
| 46 | 5 | 8.2 |
| 47 | 59 | 38 |
| 48 | 57 | 58 |
| 49 | 13 | 29 |
| 50 | 6 | 17 |
| 51 | 0.12 | 0.0035 |
| 52 | 0.027 | 0.014 |
| 53 | 0.082 | 0.073 |
| 54 | 0.93 | 0.33 |
| 55 | 0.0088 | 0.011 |
| 56 | 18 | 6.7 |
| 57 | 63 | 23 |
| 58 | 56 | 16 |
| Fasudil | 2.1 | 0.91 |

Method 2

Acute IOP Response in Lasered (Hypertensive) Eyes of Conscious Cynomolgus Monkeys Intraocular pressure (IOP) can be determined with an Alcon Pneumatonometer after light corneal anesthesia with 0.1% proparacaine. Eyes are washed with saline after each measurement. After a baseline IOP measurement, test compound is instilled in one 30 µL aliquot to the right eyes only of nine cynomolgus monkeys. Vehicle is instilled in the right eyes of six additional animals. Subsequent IOP measurements are taken at 1, 3, and 6 hours.

| | IOP Efficacy | | | |
|---|---|---|---|---|
| | Example 55 (30 ug) | | Vehicle Control | |
| Time (hrs.) | IOP Change mmHg | IOP % Change | IOP Change mmHg | IOP % Change |
| 1 | 1.0 | 1.0 | 2.4 | 10.7 |
| 3 | −8.7 | −21.6 | −0.8 | −3.0 |
| 6 | −8.9 | −22.0 | −0.5 | −1.4 |

Modes of Delivery

The compounds according to Formula I can be incorporated into various types of ophthalmic formulations for delivery. Formula I compounds may be delivered directly to the eye (for example: topical ocular drops or ointments; slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections) or systemically (for example: orally, intravenous, subcutaneous or intramuscular injections; parenterally, dermal or nasal delivery) using techniques well known by those of ordinary skill in the art. It is further contemplated that the agents of the invention may be formulated in intraocular insert or implant devices.

The compounds of Formulas I are preferably incorporated into topical ophthalmic formulations with a pH of about 4-8 for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic preparations; preservatives and tonicity agents can be incorporated.

Compounds in preferred embodiments are contained in a composition in amounts sufficient to lower IOP in patients experiencing elevated IOP and/or maintaining normal IOP levels in glaucoma patients. Such amounts are referred to herein as "an amount effective to control IOP," or more simply "an effective amount." The compounds will normally be contained in these formulations in an amount 0.01 to 5 percent by weight/volume ("w/v %"), but preferably in an amount of 0.25 to 2 w/v %. Thus, for topical presentation 1 to 2 drops of these formulations would be delivered to the surface of the eye 1 to 4 times per day, according to the discretion of a skilled clinician.

The compounds of Formula I can also be used in combination with other glaucoma treatment agents, such as, but not limited to, β-blockers, prostaglandin analogs, carbonic anhydrase inhibitors, $\alpha_2$ agonists, miotics, and neuroprotectants.

EXAMPLE FORMULATIONS

Formulation Example 1

| Ingredients | Concentration (w/v %) |
|---|---|
| Compound of Formula I | 0.01-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Formulation Example 2

| Ingredients | Concentration (w/v %) |
|---|---|
| Compound of Formula I | 0.01-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Formulation Example 3

| Ingredients | Concentration (w/v %) |
|---|---|
| Compound of Formula I | 0.01-2% |
| Guar gum | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Formulation Example 4

| Ingredients | Concentration (w/v %) |
|---|---|
| Compound of Formula I | 0.01-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. An ophthalmic pharmaceutical composition useful in the treatment of glaucoma and control of intraocular pressure, comprising an effective amount of a compound according to Formula I, or a pharmaceutically acceptable salt thereof:

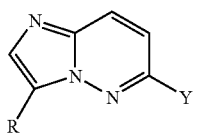

Formula I where: Y=NHR⁷, R⁷=H, $C_1$-$C_4$ alkyl optionally substituted by —$(CH_2)_n NR^5R^6$, —$(CH_2)_n OH$, or —$(CH_2)_n OR^4$; or Y=NR⁷R⁸ where R⁷ and R⁸ together form a heterocyclic ring optionally substituted by —$(CH_2)_n NR^5R^6$, or —$(CH_2)_n OH$;

R⁴=$C_1$-$C_6$ alkyl, aryl, heteroaryl;

R⁵, R⁶ independently=H, $C_1$-$C_6$ alkyl optionally substituted OH, $OR_4$, aryl, or heteroaryl;

R=

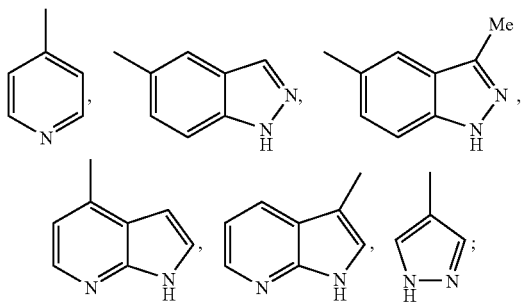

and OR n=0-4; and a pharmaceutically acceptable vehicle therefor.

2. The composition of claim 1, further comprising a compound selected from the group consisting of:
ophthalmologically acceptable preservatives, surfactants, viscosity enhancers, penetration enhancers, gelling agents, hydrophobic bases, vehicles, buffers, sodium chloride, and water.

3. The composition of claim 1, wherein said composition further comprises a glaucoma treatment agent in addition to a compound of Formula I.

4. The composition of claim 3, wherein the glaucoma treatment agent is selected from the group consisting of:
β-blockers, prostaglandin analogs, carbonic anhydrase inhibitors, $α_2$ agonists, miotics, neuroprotectants, and combinations thereof.

5. The composition of claim 1 wherein said composition comprises from 0.01 percent weight/volume to 5 percent weight/volume of said compound.

6. The composition of claim 1 wherein said composition comprises from 0.25 percent weight/volume to 2 percent weight/volume of said compound.

7. The composition of claim 1 wherein said compound is selected from the group consisting of:
3-(1H-Indazol-5-yl)-6-piperazin-1-yl-imidazo[1,2-b]pyridazine dihydrochloride, 3-(3-Methyl-1H-indazol-5-yl)-6-piperazin-1-yl-imidazo[1,2-b]pyridazine, [3-(3-methyl-1H-indazol-5-yl)- imidazo[1,2-b]pyridazine-6-yl]-piperidin-3-yl-amine trihydrochloride, 6-(1,4-Diazepan-1-yl)-3-pyridin-4-yl-imidazo[1,2-b] pyridazine hydrochloride, and 3-(3-Methyl-1H-indazol-5-yl)-6-perhydro-1,4-diazepin-1-yl-imidazo[1,2-b]pyridazine trihydrochloride.

* * * * *